US012016548B2

(12) United States Patent
Howard et al.

(10) Patent No.: US 12,016,548 B2
(45) Date of Patent: Jun. 25, 2024

(54) SUTURE ANCHOR IMPLANTATION INSTRUMENTATION SYSTEM

(71) Applicant: Howmedica Osteonics Corp., Mahwah, NJ (US)

(72) Inventors: Bryan Patrick Howard, Smithfield, UT (US); Chad Lewis, Erie, CO (US); M. Mary Sinnott, Logan, UT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 72 days.

(21) Appl. No.: 17/695,415

(22) Filed: Mar. 15, 2022

(65) Prior Publication Data
US 2022/0202411 A1 Jun. 30, 2022

Related U.S. Application Data

(63) Continuation of application No. 16/215,147, filed on Dec. 10, 2018, now Pat. No. 11,304,690, which is a
(Continued)

(51) Int. Cl.
*A61B 17/04* (2006.01)
*A61B 17/16* (2006.01)
(Continued)

(52) U.S. Cl.
CPC ...... *A61B 17/0401* (2013.01); *A61B 17/0469* (2013.01); *A61B 17/1684* (2013.01);
(Continued)

(58) Field of Classification Search
CPC . A61B 17/17; A61B 17/1739; A61B 17/0469; A61B 17/1684; A61B 2017/320052; A61B 2017/0409
See application file for complete search history.

(56) References Cited

U.S. PATENT DOCUMENTS

| 749,624 A | 1/1904 | McCullough |
| 1,308,798 A | 7/1919 | Masland |
| (Continued) | | |

FOREIGN PATENT DOCUMENTS

| CA | 2713309 A1 | 2/2011 |
| DE | 3131496 A1 | 2/1983 |
| (Continued) | | |

OTHER PUBLICATIONS

BIOMET Sports Medicine: Micromax Flex Suture Anchor, (2008).
(Continued)

*Primary Examiner* — Julian W Woo
(74) *Attorney, Agent, or Firm* — Lerner David LLP

(57) ABSTRACT

A system for implanting an anchor into bone, the system comprising a curved cannulated guide for percutaneous insertion, having a proximal end and a distal end; a flexible drill insertable through the curved guide from the proximal end to the distal end, the flexible drill having a shaft having a flexible portion; and a flexible inserter for inserting a suture anchor into a bore at the anatomical site formed by the flexible drill, the flexible inserter having a shaft having a flexible portion, wherein the flexible portions of both the flexible drill and flexible inserter include a series of discrete, interlocking segments.

20 Claims, 16 Drawing Sheets

Related U.S. Application Data continuation of application No. 15/371,914, filed on Dec. 7, 2016, now Pat. No. 10,159,478, which is a continuation of application No. 13/863,573, filed on Apr. 16, 2013, now Pat. No. 9,545,252, which is a continuation of application No. 12/821,504, filed on Jun. 23, 2010, now Pat. No. 8,439,947, which is a continuation-in-part of application No. 12/460,310, filed on Jul. 16, 2009, now Pat. No. 8,911,474.

(51) Int. Cl.
  *A61B 17/17* (2006.01)
  *A61B 17/32* (2006.01)

(52) U.S. Cl.
  CPC .......... *A61B 17/17* (2013.01); *A61B 17/1739* (2013.01); *A61B 2017/0409* (2013.01); *A61B 2017/0441* (2013.01); *A61B 2017/320052* (2013.01)

(56) References Cited

U.S. PATENT DOCUMENTS

| | | |
|---|---|---|
| 1,624,530 A | 4/1927 | Caruso |
| 2,073,903 A | 3/1937 | O'Neil |
| 2,250,434 A | 7/1941 | Dugaw |
| 2,461,947 A | 2/1949 | Weber |
| 2,515,365 A | 7/1950 | Zublin |
| 2,547,571 A | 4/1951 | Ettinger |
| 2,773,672 A | 12/1956 | Holmes et al. |
| 2,833,284 A | 5/1958 | Springer |
| 3,384,085 A | 5/1968 | Hall |
| 3,407,889 A | 10/1968 | Hjalsten et al. |
| 3,435,905 A | 4/1969 | Lazarus |
| 3,461,875 A | 8/1969 | Hall |
| 3,554,192 A | 1/1971 | Isberner |
| 3,750,671 A | 8/1973 | Hedrick |
| 3,867,932 A | 2/1975 | Huene |
| 3,892,232 A | 7/1975 | Neufeld |
| 4,212,569 A | 7/1980 | Andersson et al. |
| 4,265,231 A * | 5/1981 | Scheller, Jr. ...... A61B 17/32002 606/103 |
| 4,328,839 A | 5/1982 | Lyons et al. |
| 4,483,562 A | 11/1984 | Schoolman |
| 4,541,423 A | 9/1985 | Barber |
| 4,594,033 A | 6/1986 | Peetz et al. |
| 4,605,347 A | 8/1986 | Jodock et al. |
| 4,608,972 A | 9/1986 | Small |
| 4,611,515 A | 9/1986 | Marbourg, Jr. |
| 4,635,738 A | 1/1987 | Schillinger et al. |
| 4,646,738 A * | 3/1987 | Trott ................ A61B 17/32002 604/266 |
| 4,706,659 A | 11/1987 | Matthews et al. |
| 4,728,231 A | 3/1988 | Kunimori et al. |
| 4,748,872 A | 6/1988 | Brown |
| 4,751,922 A * | 6/1988 | DiPietropolo ......... B23Q 5/043 606/80 |
| 4,781,182 A | 11/1988 | Purnell et al. |
| 4,823,780 A | 4/1989 | Odensten et al. |
| 4,842,451 A | 6/1989 | Dugger |
| 4,863,471 A | 9/1989 | Mansat |
| 4,872,451 A | 10/1989 | Moore et al. |
| 4,946,462 A | 8/1990 | Watanabe |
| 5,002,546 A | 3/1991 | Romano |
| 5,007,911 A | 4/1991 | Baker |
| 5,030,219 A | 7/1991 | Matsen, III et al. |
| 5,037,423 A | 8/1991 | Kenna |
| 5,112,299 A | 5/1992 | Pascaloff |
| 5,122,134 A | 6/1992 | Borzone et al. |
| 5,133,720 A | 7/1992 | Greenberg |
| 5,139,520 A | 8/1992 | Rosenberg |
| 5,163,940 A | 11/1992 | Bourque |
| 5,165,494 A | 11/1992 | Barr |
| 5,186,268 A | 2/1993 | Clegg |
| 5,190,548 A | 3/1993 | Davis |
| 5,203,595 A | 4/1993 | Borzone et al. |
| RE34,293 E | 6/1993 | Goble et al. |
| 5,234,435 A | 8/1993 | Seagrave, Jr. |
| 5,269,785 A | 12/1993 | Bonutti |
| 5,273,380 A | 12/1993 | Musacchia |
| 5,300,077 A | 4/1994 | Howell |
| 5,314,429 A | 5/1994 | Goble |
| 5,320,115 A | 6/1994 | Kenna |
| 5,320,626 A | 6/1994 | Schmieding |
| 5,322,505 A | 6/1994 | Krause et al. |
| 5,330,468 A | 7/1994 | Burkhart |
| RE34,762 E | 10/1994 | Goble et al. |
| 5,374,269 A | 12/1994 | Rosenberg |
| 5,385,567 A | 1/1995 | Goble |
| 5,391,170 A | 2/1995 | McGuire et al. |
| 5,391,171 A | 2/1995 | Schmieding |
| RE34,871 E | 3/1995 | McGuire et al. |
| 5,395,188 A | 3/1995 | Bailey et al. |
| 5,403,317 A | 4/1995 | Bonutti |
| 5,409,494 A | 4/1995 | Morgan |
| 5,423,824 A | 6/1995 | Akerfeldt et al. |
| 5,437,630 A | 8/1995 | Daniel et al. |
| 5,437,675 A | 8/1995 | Wilson |
| 5,437,677 A | 8/1995 | Shearer et al. |
| 5,441,502 A | 8/1995 | Bartlett |
| 5,458,604 A | 10/1995 | Schmieding |
| 5,464,407 A | 11/1995 | McGuire |
| 5,466,243 A | 11/1995 | Schmieding et al. |
| 5,488,761 A | 2/1996 | Leone |
| 5,520,693 A | 5/1996 | McGuire et al. |
| 5,527,316 A | 6/1996 | Stone et al. |
| 5,529,580 A | 6/1996 | Kusunoki et al. |
| 5,540,703 A | 7/1996 | Barker, Jr. et al. |
| 5,570,706 A | 11/1996 | Howell |
| 5,571,111 A | 11/1996 | Aboczky |
| 5,575,819 A | 11/1996 | Amis |
| 5,584,617 A | 12/1996 | Houser |
| 5,601,550 A | 2/1997 | Esser |
| 5,601,561 A | 2/1997 | Terry et al. |
| 5,645,545 A | 7/1997 | Bryant |
| 5,658,289 A | 8/1997 | Boucher et al. |
| 5,664,914 A | 9/1997 | Taniguchi |
| 5,667,509 A | 9/1997 | Westin |
| 5,671,695 A | 9/1997 | Schroeder |
| 5,681,315 A | 10/1997 | Szabo |
| 5,681,320 A | 10/1997 | McGuire |
| 5,683,401 A | 11/1997 | Schmieding et al. |
| 5,690,660 A | 11/1997 | Kauker et al. |
| 5,690,677 A | 11/1997 | Schmieding et al. |
| 5,695,513 A | 12/1997 | Johnson et al. |
| 5,699,657 A | 12/1997 | Paulson |
| 5,700,266 A | 12/1997 | Harryman, II |
| 5,707,374 A | 1/1998 | Schmidt |
| 5,713,905 A | 2/1998 | Goble et al. |
| 5,725,530 A | 3/1998 | Popken |
| 5,732,606 A | 3/1998 | Chiang |
| 5,755,724 A | 5/1998 | Yoon |
| 5,755,731 A | 5/1998 | Grinberg |
| 5,766,221 A | 6/1998 | Benderev et al. |
| 5,782,862 A | 7/1998 | Bonutti |
| 5,788,699 A | 8/1998 | Bobst et al. |
| 5,797,918 A | 8/1998 | McGuire et al. |
| 5,820,464 A | 10/1998 | Parlato |
| 5,836,953 A | 11/1998 | Yoon |
| 5,851,208 A | 12/1998 | Trott |
| 5,888,034 A | 3/1999 | Greenberg |
| 5,895,179 A | 4/1999 | Gschwend et al. |
| 5,897,574 A | 4/1999 | Bonutti |
| 5,906,626 A | 5/1999 | Carrillo |
| 5,908,423 A | 6/1999 | Kashuba et al. |
| 5,928,244 A | 7/1999 | Tovey et al. |
| 5,941,139 A | 8/1999 | Vodehnal |
| 5,941,883 A | 8/1999 | Sklar |
| 5,947,659 A | 9/1999 | Mays |
| 5,951,559 A | 9/1999 | Burkhart |
| 5,993,451 A | 11/1999 | Burkhart |
| 6,010,515 A | 1/2000 | Swain et al. |
| 6,019,767 A | 2/2000 | Howell |

(56) References Cited

U.S. PATENT DOCUMENTS

| | | |
|---|---|---|
| 6,030,406 A | 2/2000 | Davis et al. |
| 6,053,922 A | 4/2000 | Krause et al. |
| 6,068,642 A | 5/2000 | Johnson et al. |
| 6,120,511 A | 9/2000 | Chan |
| 6,146,385 A | 11/2000 | Torrie et al. |
| 6,156,056 A | 12/2000 | Kearns et al. |
| 6,187,011 B1 | 2/2001 | Torrie |
| 6,189,422 B1 | 2/2001 | Stihl |
| 6,210,415 B1 | 4/2001 | Bester |
| 6,224,608 B1 | 5/2001 | Ciccolella et al. |
| 6,254,604 B1 | 7/2001 | Howell |
| 6,258,093 B1 | 7/2001 | Edwards et al. |
| 6,270,501 B1 | 8/2001 | Freiberg et al. |
| 6,306,138 B1 | 10/2001 | Clark et al. |
| 6,312,438 B1 | 11/2001 | Adams |
| 6,343,482 B1 | 2/2002 | Endo et al. |
| 6,352,538 B2 | 3/2002 | McGuire et al. |
| 6,358,253 B1 | 3/2002 | Torrie et al. |
| 6,364,886 B1 | 4/2002 | Sklar |
| 6,383,188 B2 | 5/2002 | Kuslich et al. |
| 6,416,517 B2 | 7/2002 | Harder et al. |
| 6,419,678 B1 | 7/2002 | Asfora |
| 6,419,684 B1 | 7/2002 | Heisler et al. |
| 6,431,801 B2 | 8/2002 | Vasudeva et al. |
| 6,436,100 B1 | 8/2002 | Berger |
| 6,440,138 B1 | 8/2002 | Reiley et al. |
| 6,440,141 B1 | 8/2002 | Philippon |
| 6,447,518 B1 | 9/2002 | Krause et al. |
| 6,474,425 B1 | 11/2002 | Truax et al. |
| 6,478,800 B1 | 11/2002 | Fraser et al. |
| 6,494,272 B1 | 12/2002 | Eppink et al. |
| 6,558,386 B1 * | 5/2003 | Cragg .................. A61F 2/4465 606/279 |
| 6,558,390 B2 | 5/2003 | Cragg |
| 6,575,979 B1 | 6/2003 | Cragg |
| 6,610,080 B2 | 8/2003 | Morgan |
| 6,712,822 B2 | 3/2004 | Re et al. |
| 6,740,090 B1 | 5/2004 | Cragg et al. |
| 6,743,239 B1 | 6/2004 | Kuehn et al. |
| 6,746,451 B2 | 6/2004 | Middleton et al. |
| 6,780,188 B2 | 8/2004 | Clark et al. |
| 6,783,533 B2 | 8/2004 | Green et al. |
| 6,790,210 B1 | 9/2004 | Cragg et al. |
| 6,805,697 B1 | 10/2004 | Helm et al. |
| 6,824,552 B2 | 11/2004 | Robison et al. |
| 6,830,570 B1 | 12/2004 | Frey et al. |
| 6,863,672 B2 | 3/2005 | Reiley et al. |
| 6,874,978 B2 | 4/2005 | Gongola |
| 6,878,150 B1 | 4/2005 | McGuire et al. |
| 6,893,445 B1 | 5/2005 | Revie et al. |
| 6,899,716 B2 | 5/2005 | Cragg |
| 6,921,403 B2 | 7/2005 | Cragg et al. |
| 6,923,811 B1 | 8/2005 | Carl et al. |
| 6,923,814 B1 | 8/2005 | Hildebrand et al. |
| 6,936,052 B2 | 8/2005 | Gellman et al. |
| 6,960,214 B2 | 11/2005 | Burkinshaw |
| 6,994,725 B1 | 2/2006 | Goble |
| 7,008,431 B2 | 3/2006 | Simonson |
| 7,018,144 B2 | 3/2006 | Sasagawa et al. |
| 7,025,770 B2 | 4/2006 | McGuire et al. |
| 7,029,479 B2 | 4/2006 | Tallarida et al. |
| 7,041,107 B2 | 5/2006 | Pohjonen et al. |
| 7,060,073 B2 | 6/2006 | Frey et al. |
| 7,067,132 B2 | 6/2006 | Grabstein et al. |
| 7,077,863 B2 | 7/2006 | Schmieding et al. |
| 7,087,058 B2 | 8/2006 | Cragg |
| 7,204,839 B2 | 4/2007 | Dreyfuss et al. |
| 7,235,091 B2 | 6/2007 | Thornes |
| 7,241,297 B2 | 7/2007 | Shaolian et al. |
| 7,258,692 B2 | 8/2007 | Thelen et al. |
| 7,261,016 B2 | 8/2007 | Miller |
| 7,309,338 B2 | 12/2007 | Cragg |
| 7,326,215 B2 | 2/2008 | Myers et al. |
| 7,331,263 B2 | 2/2008 | Erickson et al. |
| 7,357,804 B2 | 4/2008 | Binder, Jr. et al. |
| 7,488,322 B2 | 2/2009 | Brunnett et al. |
| 7,488,329 B2 | 2/2009 | Thelen et al. |
| 7,494,490 B2 | 2/2009 | Justin |
| 7,500,977 B2 | 3/2009 | Assell et al. |
| 7,503,920 B2 | 3/2009 | Siegal |
| 7,563,266 B2 | 7/2009 | Camino et al. |
| 7,585,300 B2 | 9/2009 | Cha |
| 7,604,636 B1 | 10/2009 | Walters et al. |
| 7,611,521 B2 | 11/2009 | Lubbers et al. |
| 7,621,912 B2 | 11/2009 | Harms et al. |
| 7,621,940 B2 | 11/2009 | Harms et al. |
| 7,651,509 B2 | 1/2010 | Bojarski et al. |
| 7,651,515 B2 | 1/2010 | Mack et al. |
| 7,666,189 B2 | 2/2010 | Gerber et al. |
| 7,776,049 B1 | 8/2010 | Curran et al. |
| 7,803,173 B2 | 9/2010 | Burkhart et al. |
| 7,875,057 B2 | 1/2011 | Cook et al. |
| 7,875,058 B2 | 1/2011 | Holmes, Jr. |
| 7,879,037 B2 | 2/2011 | Brunnett et al. |
| 7,892,235 B2 | 2/2011 | Ellis |
| 7,901,431 B2 | 3/2011 | Shumnas |
| 7,909,547 B2 | 3/2011 | Jordan et al. |
| 7,918,874 B2 | 4/2011 | Siegal |
| 7,959,641 B2 | 6/2011 | Sorensen et al. |
| 7,963,967 B1 | 6/2011 | Woods |
| 7,981,117 B2 | 7/2011 | Newton et al. |
| 7,981,140 B2 | 7/2011 | Burkhart |
| 8,002,733 B2 | 8/2011 | Kraft et al. |
| 8,043,253 B2 | 10/2011 | Kraft et al. |
| 8,057,500 B2 | 11/2011 | Mitusina |
| 8,070,750 B2 | 12/2011 | Wenstrom, Jr. et al. |
| 8,109,700 B2 | 2/2012 | Jordan et al. |
| 8,114,088 B2 | 2/2012 | Miller |
| 8,123,750 B2 | 2/2012 | Norton et al. |
| 8,128,640 B2 | 3/2012 | Harris et al. |
| 8,133,231 B2 | 3/2012 | Martinek et al. |
| 8,162,997 B2 | 4/2012 | Struhl |
| 8,172,846 B2 | 5/2012 | Brunnett et al. |
| 8,231,674 B2 | 7/2012 | Albertorio et al. |
| 8,267,959 B2 | 9/2012 | Fallman |
| 8,287,539 B2 | 10/2012 | Nelson et al. |
| 8,287,541 B2 | 10/2012 | Nelson et al. |
| 8,312,942 B2 | 11/2012 | Ho et al. |
| 8,343,187 B2 | 1/2013 | Lamson et al. |
| 8,366,713 B2 | 2/2013 | Long et al. |
| 8,394,129 B2 | 3/2013 | Morgenstern Lopez et al. |
| 8,398,678 B2 | 3/2013 | Baker et al. |
| 8,409,253 B2 | 4/2013 | Stone et al. |
| 8,439,976 B2 | 5/2013 | Albertorio et al. |
| 8,512,340 B2 | 8/2013 | Easley et al. |
| 8,518,087 B2 | 8/2013 | Lopez et al. |
| 8,556,911 B2 | 10/2013 | Mehta et al. |
| 8,568,413 B2 | 10/2013 | Mazur et al. |
| 8,591,578 B2 | 11/2013 | Albertorio et al. |
| 8,597,333 B2 | 12/2013 | Morgenstern Lopez et al. |
| 8,623,051 B2 | 1/2014 | Bojarski et al. |
| 8,663,324 B2 | 3/2014 | Schmieding et al. |
| 9,072,530 B2 | 7/2015 | Mehta et al. |
| 9,101,373 B2 | 8/2015 | Norton et al. |
| 9,232,954 B2 | 1/2016 | Steiner et al. |
| 9,795,398 B2 | 10/2017 | Steiner et al. |
| 10,022,131 B1 | 7/2018 | Burley et al. |
| 2002/0019635 A1 | 2/2002 | Wenstrom et al. |
| 2002/0022847 A1 | 2/2002 | Ray et al. |
| 2002/0183758 A1 | 12/2002 | Middleton et al. |
| 2002/0188301 A1 | 12/2002 | Dallara et al. |
| 2003/0176919 A1 | 9/2003 | Schmieding |
| 2003/0220646 A1 | 11/2003 | Thelen et al. |
| 2003/0233098 A1 | 12/2003 | Markworth |
| 2004/0010264 A1 | 1/2004 | Acker et al. |
| 2004/0030346 A1 | 2/2004 | Frey et al. |
| 2004/0073227 A1 | 4/2004 | Dreyfuss et al. |
| 2004/0073306 A1 | 4/2004 | Eichhorn et al. |
| 2004/0092933 A1 | 5/2004 | Shaolian et al. |
| 2004/0149093 A1 | 8/2004 | Tang |
| 2004/0193168 A1 | 9/2004 | Long et al. |
| 2004/0193217 A1 | 9/2004 | Lubbers et al. |
| 2004/0208717 A1 | 10/2004 | Greenhalgh |
| 2004/0260300 A1 | 12/2004 | Gorensek et al. |

(56) References Cited

U.S. PATENT DOCUMENTS

| | | |
|---|---|---|
| 2004/0267277 A1 | 12/2004 | Zannis et al. |
| 2005/0015153 A1 | 1/2005 | Goble et al. |
| 2005/0054953 A1 | 3/2005 | Ryan et al. |
| 2005/0070906 A1 | 3/2005 | Clark et al. |
| 2005/0080400 A1 | 4/2005 | Corcoran et al. |
| 2005/0137600 A1 | 6/2005 | Jacobs et al. |
| 2005/0137601 A1 | 6/2005 | Assell et al. |
| 2005/0143741 A1 | 6/2005 | Timmermans et al. |
| 2005/0177168 A1 | 8/2005 | Brunnett et al. |
| 2005/0187537 A1 | 8/2005 | Loeb et al. |
| 2005/0203527 A1 | 9/2005 | Carrison et al. |
| 2005/0228399 A1 | 10/2005 | Kubo et al. |
| 2005/0261604 A1 | 11/2005 | Stephens et al. |
| 2006/0004369 A1 | 1/2006 | Patel et al. |
| 2006/0015110 A1 | 1/2006 | Pepper |
| 2006/0074434 A1 | 4/2006 | Wenstrom et al. |
| 2006/0100631 A1 | 5/2006 | Sullivan et al. |
| 2006/0178748 A1 | 8/2006 | Dinger et al. |
| 2006/0293689 A1 | 12/2006 | Miller et al. |
| 2007/0010843 A1 | 1/2007 | Green |
| 2007/0043376 A1 | 2/2007 | Leatherbury et al. |
| 2007/0093840 A1 | 4/2007 | Pacelli et al. |
| 2007/0191853 A1 | 8/2007 | Stone |
| 2007/0213734 A1 | 9/2007 | Bleich et al. |
| 2007/0213735 A1 | 9/2007 | Saadat et al. |
| 2007/0225721 A1 | 9/2007 | Thelen et al. |
| 2007/0233151 A1 | 10/2007 | Chudik |
| 2007/0260259 A1 | 11/2007 | Fanton et al. |
| 2007/0276392 A1 | 11/2007 | Beyar et al. |
| 2007/0288031 A1 | 12/2007 | Dreyfuss et al. |
| 2008/0027457 A1 | 1/2008 | Dienst et al. |
| 2008/0058816 A1 | 3/2008 | Philippon et al. |
| 2008/0065080 A1 | 3/2008 | Assell et al. |
| 2008/0065092 A1 | 3/2008 | Assell et al. |
| 2008/0071282 A1 | 3/2008 | Assell et al. |
| 2008/0109037 A1 | 5/2008 | Steiner et al. |
| 2008/0114364 A1 | 5/2008 | Goldin et al. |
| 2008/0132932 A1 | 6/2008 | Hoeppner et al. |
| 2008/0140078 A1 | 6/2008 | Nelson et al. |
| 2008/0147071 A1 | 6/2008 | Serra et al. |
| 2008/0154275 A1 | 6/2008 | Assell et al. |
| 2008/0161814 A1 | 7/2008 | McAllister et al. |
| 2008/0167660 A1 | 7/2008 | Moreau et al. |
| 2008/0188854 A1 | 8/2008 | Moser |
| 2008/0188935 A1 | 8/2008 | Saylor et al. |
| 2008/0243163 A1 | 10/2008 | Masseglia et al. |
| 2008/0249481 A1 | 10/2008 | Crainich et al. |
| 2008/0275453 A1 | 11/2008 | Lafosse et al. |
| 2008/0306483 A1 | 12/2008 | Iannarone |
| 2009/0012526 A1 | 1/2009 | Fletcher |
| 2009/0018654 A1 | 1/2009 | Schmieding et al. |
| 2009/0024130 A1 | 1/2009 | Lombardo |
| 2009/0076514 A1 | 3/2009 | Haines |
| 2009/0099554 A1 | 4/2009 | Forster et al. |
| 2009/0105775 A1 | 4/2009 | Mitchell et al. |
| 2009/0131940 A1 | 5/2009 | Brunnett et al. |
| 2009/0138015 A1 | 5/2009 | Conner et al. |
| 2009/0143784 A1 | 6/2009 | Petersen et al. |
| 2009/0149858 A1 | 6/2009 | Fanelli et al. |
| 2009/0149890 A1 | 6/2009 | Martin |
| 2009/0157081 A1 | 6/2009 | Homan et al. |
| 2009/0160112 A1 | 6/2009 | Ostrovsky |
| 2009/0171359 A1 | 7/2009 | Sterrett |
| 2009/0194446 A1 | 8/2009 | Miller et al. |
| 2009/0198258 A1 | 8/2009 | Workman |
| 2009/0216236 A1 | 8/2009 | Re |
| 2009/0216238 A1 | 8/2009 | Stark |
| 2009/0216243 A1 | 8/2009 | Re |
| 2009/0222013 A1 | 9/2009 | Graf et al. |
| 2009/0248029 A1 | 10/2009 | Paulos |
| 2009/0306671 A1 | 12/2009 | McCormack et al. |
| 2009/0312763 A1 | 12/2009 | McCormack et al. |
| 2009/0326538 A1 | 12/2009 | Sennett et al. |
| 2010/0049196 A1 | 2/2010 | Re |
| 2010/0049200 A1 | 2/2010 | Re |
| 2010/0049202 A1 | 2/2010 | Re |
| 2010/0049203 A1 | 2/2010 | Re |
| 2010/0057045 A1 | 3/2010 | Albritton, IV et al. |
| 2010/0076440 A1 | 3/2010 | Pamichev et al. |
| 2010/0082033 A1 | 4/2010 | Germain |
| 2010/0121332 A1 | 5/2010 | Crainich et al. |
| 2010/0121333 A1 | 5/2010 | Crainich et al. |
| 2010/0152739 A1 | 6/2010 | Sidebotham et al. |
| 2010/0160962 A1 | 6/2010 | Dreyfuss et al. |
| 2010/0191241 A1 | 7/2010 | McCormack et al. |
| 2010/0241121 A1 | 9/2010 | Logan et al. |
| 2010/0249786 A1 | 9/2010 | Schmieding et al. |
| 2010/0262146 A1 | 10/2010 | Tulkis |
| 2010/0286694 A1 | 11/2010 | Rio et al. |
| 2010/0292731 A1 | 11/2010 | Gittings et al. |
| 2011/0015674 A1 | 1/2011 | Howard et al. |
| 2011/0015675 A1 | 1/2011 | Howard et al. |
| 2011/0022083 A1 | 1/2011 | DiMatteo et al. |
| 2011/0022084 A1 | 1/2011 | Sengun et al. |
| 2011/0087247 A1 | 4/2011 | Fung et al. |
| 2011/0106089 A1 | 5/2011 | Brunnett et al. |
| 2011/0152927 A1 | 6/2011 | Deng et al. |
| 2011/0208194 A1 | 8/2011 | Steiner et al. |
| 2011/0218538 A1* | 9/2011 | Sherman ............ A61B 17/1631 |
| | | 219/121.64 |
| 2011/0270278 A1 | 11/2011 | Overes et al. |
| 2011/0270293 A1 | 11/2011 | Malla et al. |
| 2011/0319896 A1 | 12/2011 | Papenfuss et al. |
| 2012/0004672 A1 | 1/2012 | Giap et al. |
| 2012/0053641 A1 | 3/2012 | Meridew |
| 2012/0109142 A1 | 5/2012 | Dayan |
| 2012/0109156 A1 | 5/2012 | Overes et al. |
| 2012/0109194 A1 | 5/2012 | Miller et al. |
| 2012/0123474 A1 | 5/2012 | Zajac et al. |
| 2012/0150203 A1 | 6/2012 | Brady et al. |
| 2012/0150301 A1 | 6/2012 | Gamache et al. |
| 2012/0197271 A1 | 8/2012 | Astorino et al. |
| 2012/0203231 A1 | 8/2012 | Long et al. |
| 2012/0203288 A1 | 8/2012 | Lange et al. |
| 2012/0209325 A1 | 8/2012 | Gagliano et al. |
| 2012/0253355 A1 | 10/2012 | Murray et al. |
| 2012/0265205 A1 | 10/2012 | Steiner et al. |
| 2012/0290002 A1 | 11/2012 | Astorino |
| 2012/0290006 A1 | 11/2012 | Collins et al. |
| 2013/0023929 A1 | 1/2013 | Sullivan et al. |
| 2013/0053897 A1 | 2/2013 | Brown et al. |
| 2013/0072989 A1 | 3/2013 | Overes et al. |
| 2013/0085568 A1 | 4/2013 | Smith et al. |
| 2013/0096611 A1 | 4/2013 | Sullivan |
| 2013/0096612 A1 | 4/2013 | Zajac et al. |
| 2013/0110165 A1 | 5/2013 | Burkhart et al. |
| 2013/0158601 A1 | 6/2013 | Stone et al. |
| 2013/0165972 A1 | 6/2013 | Sullivan |
| 2013/0237997 A1 | 9/2013 | Arai et al. |
| 2013/0238025 A1 | 9/2013 | Howard et al. |
| 2013/0245700 A1 | 9/2013 | Choinski |
| 2013/0268000 A1 | 10/2013 | Harner et al. |
| 2013/0296931 A1 | 11/2013 | Sengun |
| 2013/0317544 A1 | 11/2013 | Ferguson et al. |
| 2013/0345749 A1 | 12/2013 | Sullivan et al. |
| 2014/0107657 A1 | 4/2014 | Norton et al. |
| 2014/0114312 A1 | 4/2014 | Krause |

FOREIGN PATENT DOCUMENTS

| | | |
|---|---|---|
| DE | 8903079 U1 | 5/1989 |
| DE | 4231101 A1 | 3/1994 |
| DE | 4243715 A1 | 7/1994 |
| DE | 19503504 A1 | 3/1996 |
| DE | 202009007979 U1 | 8/2009 |
| EP | 153831 A2 | 9/1985 |
| EP | 253526 A1 | 1/1988 |
| EP | 0440371 A1 | 8/1991 |
| EP | 1155776 A2 | 11/2001 |
| EP | 1174584 A2 | 1/2002 |
| EP | 1369089 A2 | 12/2003 |
| EP | 1398455 A2 | 3/2004 |
| EP | 2286742 A1 | 2/2011 |
| FR | 1166884 A | 11/1958 |

(56) References Cited

FOREIGN PATENT DOCUMENTS

| FR | 2606996 A1 | 5/1988 |
|---|---|---|
| FR | 2676638 A1 | 11/1992 |
| GB | 2093353 A | 9/1982 |
| WO | 9704908 A1 | 2/1997 |
| WO | 0024327 A2 | 5/2000 |
| WO | 0044291 A1 | 8/2000 |
| WO | 0128457 A1 | 4/2001 |
| WO | 0160268 A1 | 8/2001 |
| WO | 03007861 A1 | 1/2003 |
| WO | 03086221 A1 | 10/2003 |
| WO | 2004092531 A2 | 10/2004 |
| WO | 2007/010389 A1 | 1/2007 |
| WO | 2008128075 A1 | 10/2008 |
| WO | 2009105880 A1 | 9/2009 |

OTHER PUBLICATIONS

International Search Report PCT/US2010/042264, dated Sep. 30, 2010.
European Search Report, EP 10173568, dated Nov. 30, 2010.
Chen et al., Journal of Orthopaedic Research, pp. 1432-1438, Nov. 2009.
Chen et al., Poster No. 538, 54th Annual Meeting of the Orthopaedic Research Society, San Francisco, CA Mar. 2008.
HHS Tube, Fort Wayne Metals Research Products Corp., 2009, 2 pages.
Cole et al., American Journal of Sports Medicine, vol. XX, No. X, Apr. 2011, 10 pages.
Medtronic, The VISAO High-Speed Otologic Drill Catalog, 2007, 12 pages.
Insall et al., "Intra-Articular Surgery for Degenerative Arthritis of the Knee," The Journal of Bone and Joint Surgery, vol. 49B, No. 2, pp. 211-228, May 1967.
Chen et al., "A Comparative Study of Drilling Versus Microfracture for Cartilage Repair in a Rabbit Model," European Cells and Materials, vol. 16, Supp. 4, p. 7, 2008.
Steiner et al., U.S. Appl. No. 13/085,882, filed Apr. 13, 2011, titled "Flexible ACL Instrumentation, Kit and Method".
Long et al., U.S. Appl. No. 13/368,730, filed Feb. 8, 2012, titled "Flexible Microdrilling Instrumentation, Kits and Methods".
Extended European Search Report for Application No. EP 12164104 dated Jul. 11, 2012.
Burkinshaw, U.S. Appl. No. 60/418,545, filed Oct. 15, 2002.
European Search Report for Application No. 10173568.6 dated Feb. 9, 2015.

* cited by examiner

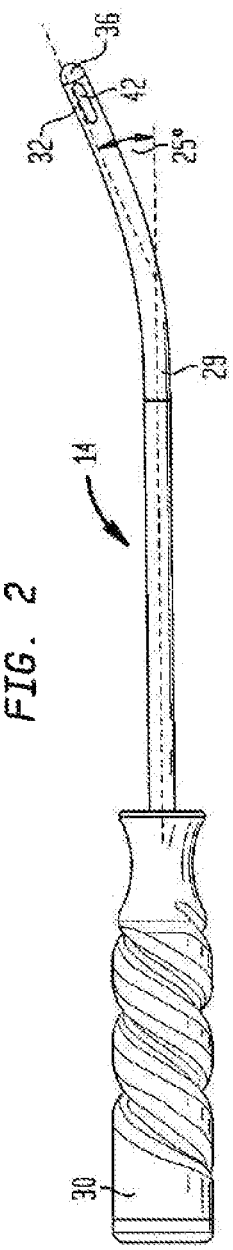

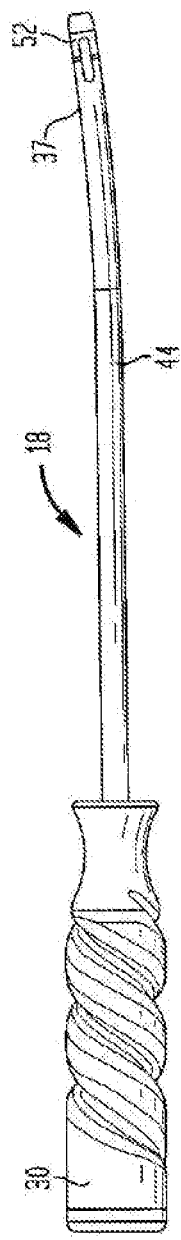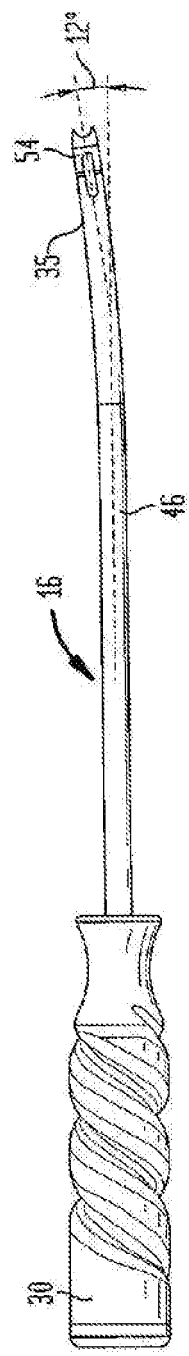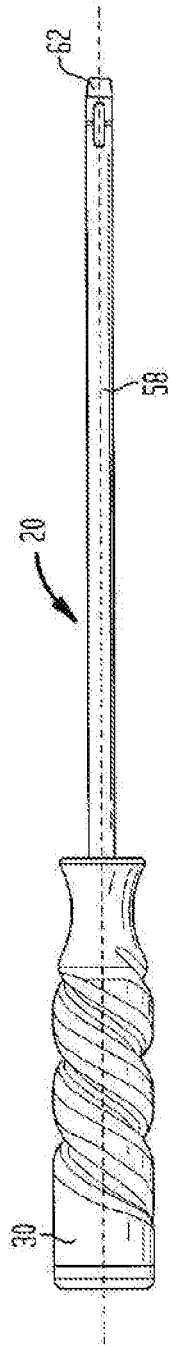

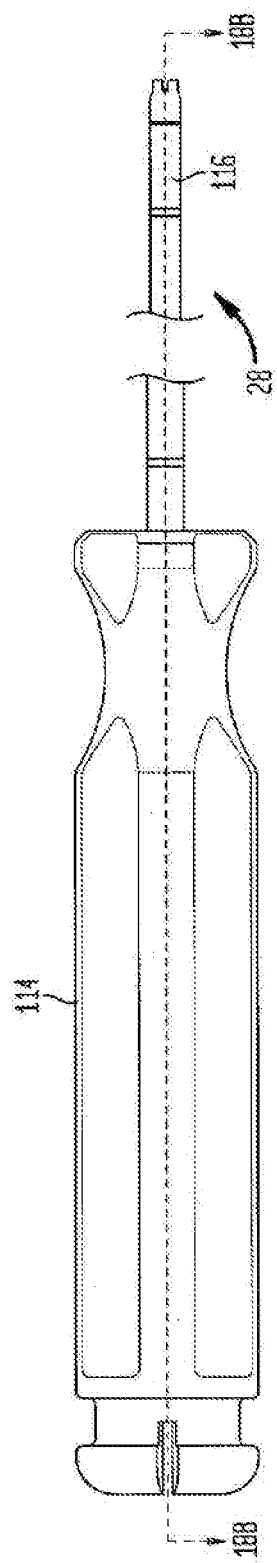
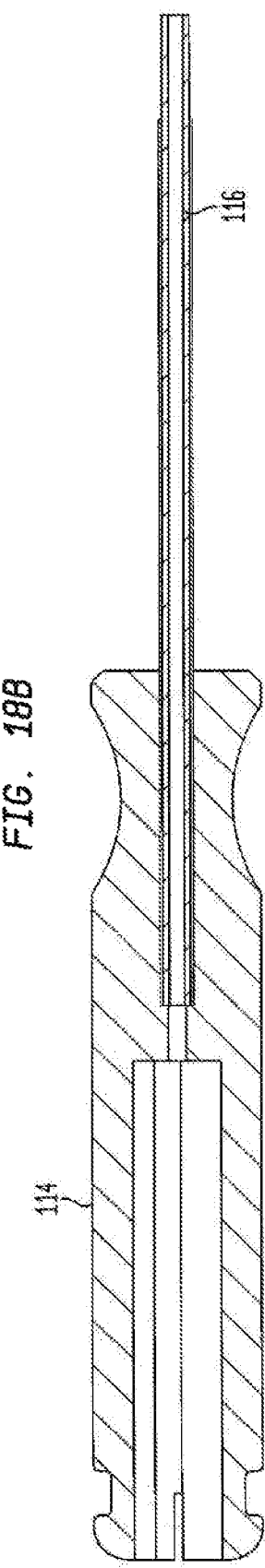

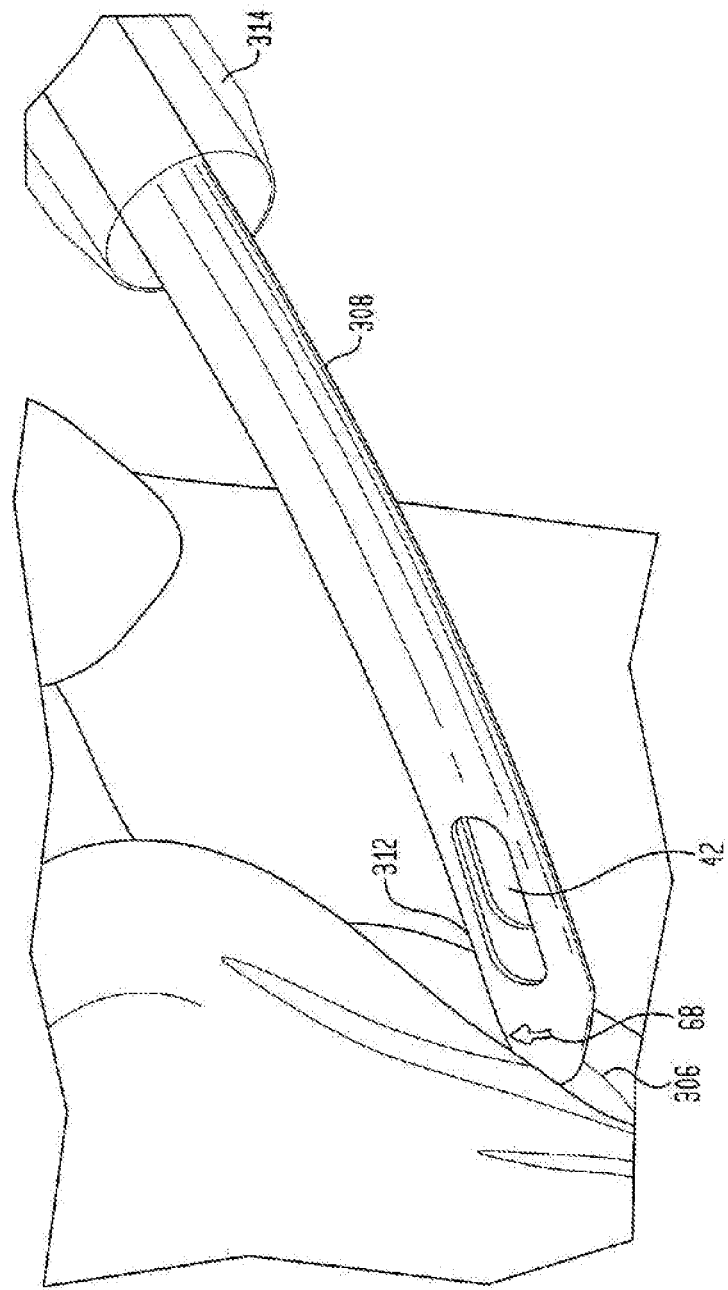

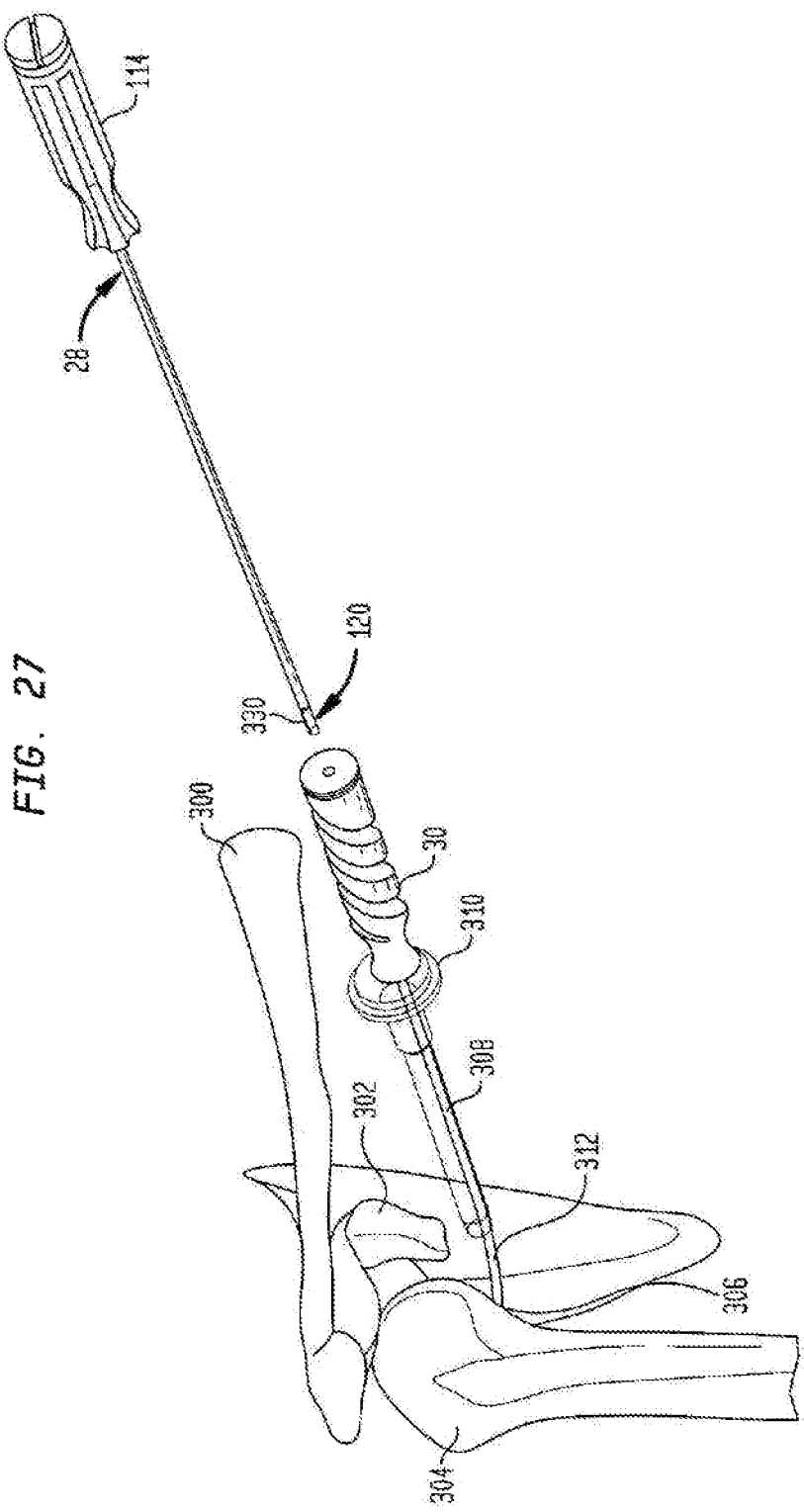

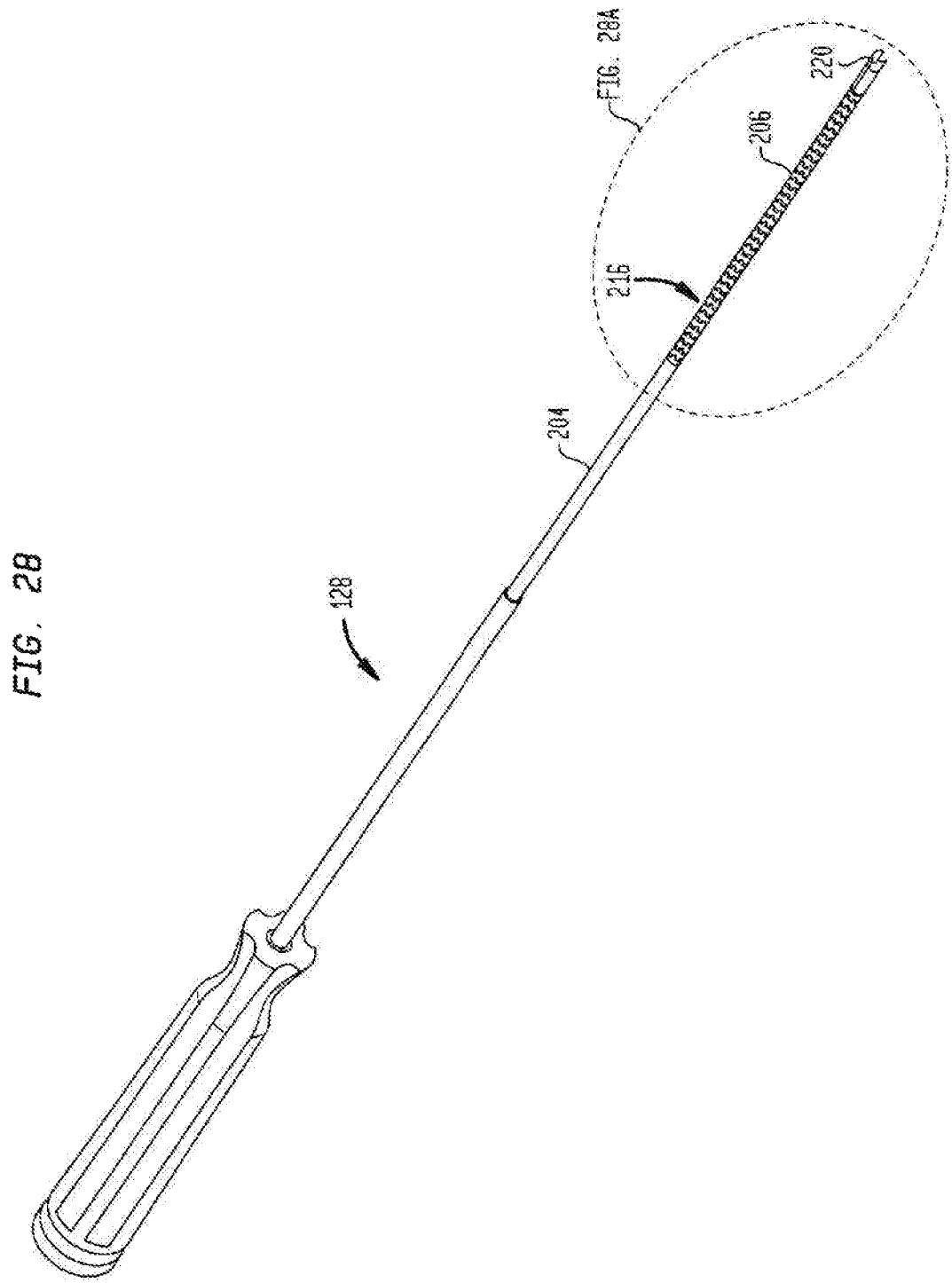

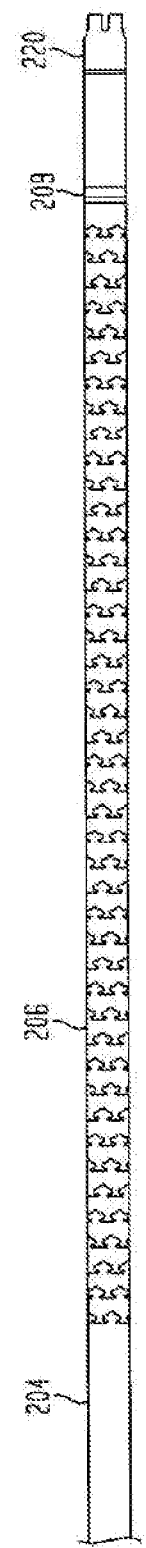

SUTURE ANCHOR IMPLANTATION INSTRUMENTATION SYSTEM

CROSS-REFERENCE TO RELATED APPLICATIONS

This application is a continuation of U.S. application Ser. No. 16/215,147, filed Dec. 10, 2018, now U.S. Pat. No. 11,304,690, which is a continuation of U.S. patent application Ser. No. 15/371,914, filed Dec. 7, 2016 now U.S. Pat. No. 10,159,478, which is a continuation of U.S. patent application Ser. No. 13/863,573, filed Apr. 16, 2013, now U.S. Pat. No. 9,545,252, which is a continuation of U.S. patent application Ser. No. 12/821,504, filed Jun. 23, 2010, now U.S. Pat. No. 8,439,947, which is a continuation-in-part of U.S. patent application Ser. No. 12/460,310, filed Jul. 16, 2009, now U.S. Pat. No. 8,911,474, the disclosures of which are hereby incorporated herein by reference.

BACKGROUND OF THE INVENTION

Various shoulder injuries may result from dislocations, falling, throwing, or lifting. A common shoulder injury includes the separation of the glenoid labrum from the glenoid. For example, a Bankart lesion results from a labral tear that occurs in the anterioinferior region of the glenoid socket when the shoulder dislocates. A superior labral anterior posterior (SLAP) lesion typically occurs from throwing injuries, where the tear occurs at the superior region of the glenoid socket where the biceps tendon attaches to the shoulder. These injuries result in pain and instability of the shoulder joints.

Arthroscopic stabilization for surgical treatment of shoulder instability has grown in popularity over the past decade. In particular, labral anchors have been employed to repair torn labrum tissue. For example, a labral anchor may be inserted into the glenoid, and a suture material that is attached to the labral anchor is used to reattach the torn labral tissue to the glenoid.

BRIEF SUMMARY OF THE INVENTION

In one embodiment, the present invention may include an apparatus adapted for use with a surgical cannula for inserting a suture anchor into an internal anatomical site may include a curved hollow guide for accessing an internal anatomical site, having a proximal end and a distal end; a flexible oburator insertable through the curved guide from the proximal end to the distal end; a flexible drill insertable through the curved guide from the proximal end to the distal end; and a flexible inserter for inserting a suture anchor into a bore at the anatomical site formed by the flexible drill, wherein the flexible drill and flexible inserter each may include a shaft having a flexible portion including a plurality of laser cuts. The shafts of the flexible drill and flexible inserter may further be substantially cannulated and may include a thickness between an outer surface and an inner surface. Furthermore, the plurality of laser cuts of at least one of the flexible portions of the flexible drill and flexible inserter may extend circumferentially around the outer surface of the shaft and may extend at least partially through the thickness of the shaft. Moreover, the plurality of laser cuts may extend completely through the thickness of the shaft of at least one of the flexible drill and flexible inserter, such that the flexible portions of the flexible drill and flexible inserter may be discrete, interlocking segments. Additionally, the shafts of the flexible drill and the flexible inserter may be constructed from a material comprising hypodermic tubing, polymer, or stainless steel.

In another embodiment, the present invention may be a system for implanting an anchor into bone, the system comprising a curved cannulated guide for percutaneous insertion, having a proximal end and a distal end, a flexible obturator insertable through the curved guide from the proximal end to the distal end, a flexible obturator insertable through the curved guide from the proximal end to the distal end, a flexible drill insertable through the curved guide from the proximal end to the distal end, and a flexible inserter for inserting a suture anchor into a bore at the anatomical site formed by the flexible drill.

In yet another embodiment, the present invention may be a system for implanting an anchor into bone, the system comprising a cannulated guide comprising a proximal end, a distal end positionable proximate a bone, and a curved shaft extending between the proximal and distal ends; a drill comprising a proximal end configured to receive torque, a distal rotary drilling head, and a shaft extending between the proximal end and the rotary drilling head, wherein the shaft comprises a flexible portion and permits passage of the rotary drilling head through the shaft of the cannulated guide; and wherein one of the drill and the cannulated guide comprises a stop feature shaped to interface with the other of the drill and the cannulated guide to adjustably control a maximum range of motion of the rotary drilling head through the cannulated guide.

In a further embodiment, the present invention may be a system for implanting an anchor into bone, the system comprising a curved cannulated guide for percutaneous insertion, having a proximal end and a distal end; a flexible drill insertable through the curved guide from the proximal end to the distal end, the flexible drill having a shaft having a flexible portion; and a flexible inserter for inserting a suture anchor into a bore at the anatomical site formed by the flexible drill, the flexible inserter having a shaft having a flexible portion, wherein the flexible portions of both the flexible drill and flexible inserter include a series of discrete, interlocking segments. The flexible portions may further include discrete, interlocking segments which may be constructed from a material such as hypodermic tubing, stainless steel, polymer, or the like. The discrete, interlocking segments may further be constructed from a solid, continuous length of material. These segments may also be constructed from the solid, continuous length of material by a laser cutting process, or the like.

The curved labrum instrumentation of the present invention will make the existing SLAP and Bankart surgical procedures, in particular, the 5 and 6 o'clock position repairs, easier to perform by making it possible to achieve anchor hole vectors that are much closer to perpendicular with the surfaces of the scapular glenoid rim. This improved insertion vector will lessen the probability of anchor back out and thereby improve the quality of the surgical repair.

The instrumentation system of the present invention includes, in one embodiment, four curved tubular guides and a straight tubular guide with each guide including a cannulated handle, a hollow shaft, and a parabolic-shaped distal end aperture. The curved guides may be provided at any angle between and including 0 and 90 degrees. For example, the curved guides of the system may have a curved angle of 12 or 25 degrees, in addition to the straight guide having no curved angle (i.e., 0 degrees). As to the curved guides, the parabolic-shaped distal aperture may have one of a standard or rotated orientation. A standard orientation may have the parabolic aperture aligned with the curve of the guide, while a rotated orientation may designate that the parabolic aperture is offset from the curve of the guide, for example, by 90 degrees. Of course, a parabolic aperture on a straight guide would not have an orientation as to a curved angle. The system also may include at least one obturator which is placed at the distal end of each guide with the obturator shaped as either a bullet or a trocar, or one of each may be included. A drill is provided for insertion through any of the guides for forming a pilot hole in the glenoid rim for receiving a suture anchor. The drill and the obturators may have flexible shafts allowing the tips to traverse the curved portions of the curved guides.

The handle portion of each guide may provide the user with a place to grasp the instrument during use and, in the case of using the drill, to provide a geometry that will prevent the user from drilling past a set drill depth. The guide handle is also cannulated to allow for the insertion of the flexible obturators, the flexible drill, and a flexible inserter for the suture anchor.

The shaft portion of the guides may incorporate a curve at the distal end that achieves about 0 to about 90 degrees of bend, and specifically about 0 to about 25 degrees of bend, over a linear shaft distance of, for example, 1-3 inches. The distal tip of the guide shafts may incorporate viewing windows that allow visual access to the drill and anchor inserter during surgical procedures and also has a "parabolic" design end aperture that is designed to physically mate with anatomical features of the glenoid to ensure proper and secure guide positioning. A laser mark may also be located adjacent the distal tip to provide an alignment feature to be used with laser marks on the drill and inserter for depth gauging purposes.

Flexible obturators may be provided which, in one embodiment, consist of a titanium handle, a flexible nitinol shaft, and a titanium tip. A rounded tip obturator utilizes a bullet-shaped tip, which functions to protect the seal of a cannula (if used), and/or surrounding tissue, from the "parabolic" shaped edges of the 0°, 12° and 25° guides during the insertion process of the guides into the joint space. A trocar tip obturator utilizes a trocar tip, which tip functions to puncture tissue during the insertion of any of the guides into the joint space during percutaneous surgical approaches. Both obturators are designed to be reusable instruments and to be compatible with any of the suture anchor guides.

A flexible drill may be provided which may consist of three sections; (1) a proximal shaft, (2) a central shaft, and (3) a drill tip. The proximal and central shafts may be of a continuous piece of material which is laser welded to the drill tip, or alternatively the three sections of this instrument may be separate and laser welded together, though other methods of attachment known in the art may be used. The proximal and central shaft portions consist of, for example machined hypodermic tubing and functions to allow the attachment of an orthopedic power drill driver to the proximal end and include geometry that allows the user to adjust the drilling depth. The center portion may, in one embodiment, incorporate a flexible laser cut feature near its distal end that allows the distal portion to flex without elastically or plastically deforming the material and thereby navigate the bend in the guide shaft. In a first embodiment, this may be accomplished via dovetail-shaped cuts which divide the tube into discrete yet interlocking segments. The drill tip consists of a drill bit made of machined rod stock and is designed to drill a hole of appropriate depth and diameter in the surface of the scapular glenoid rim for the purpose of inserting a suture anchor such as a Stryker 3.5 mm Twin-Loop™ suture anchor.

A flexible suture anchor inserter may also be provided which may consist of a polymer handle over molded onto a flexible shaft assembly constructed of, for example, polymer and/or stainless steel. The shaft portion is capable of withstanding enough axial compression to allow the suture anchor to be inserted into the drilled pilot hole without buckling. The shaft is also flexible enough to facilitate anchor insertion through the curved guide. The distal end of the inserter may be rigid and substantially straight to remain straight as the anchor is maneuvered into the bore hole. In one example, the distal end is made of metal, such as stainless steel, or another equally rigid material. The shaft portion may be of solid construction which may be elastically bendable. Alternatively, the shaft portion may be of a construction similar to the shaft of the flexible drill, as discussed above, and may thus be constructed of interlocking segments which are formed in a similar fashion as the shaft of the flexible drill.

In a further embodiment, a method of performing a surgical technique may comprise inserting a curved hollow guide, and a flexible obturator positioned within the curved hollow guide, for accessing an internal anatomical site; removing the flexible obturator once the curved hollow guide is in place, inserting a flexible drill into the curved hollow guide; drilling a hole at the internal anatomical site; removing the flexible drill from the curved hollow guide; inserting a flexible inserter into the curved hollow guide having a suture anchor engaged to the distal end of the flexible inserter; inserting the suture anchor into the hole at the internal anatomical site; and removing the curved hollow guide and flexible inserter from the internal anatomical site. In an alternative embodiment, a cannula may be used through which the curved hollow guide may pass to reach the internal anatomical site.

The surgical techniques employed during the use of the instrumentation of the present invention are similar to those already used for SLAP and Bankart surgical repairs. The curved geometry of this instrumentation makes these surgical procedures easier to perform and more reliable and repeatable. Initially, in a first embodiment, a cannula, such as a Stryker Corp. 8 mm DriLok™ cannula, or any suitable cannula known in the art, may be placed in the shoulder in a standard fashion. Then an appropriate flexible obturator is placed inside an appropriate curved guide and the curved guide is then inserted through the cannula and into the joint capsule. Alternatively, in another embodiment, the appropriate guide can be inserted percutaneously into the joint capsule, without the use of a cannula, and may be used with a trocar tip obturator, for example. Once the guide is in place, the obturator is removed from the curved guide. A flexible drill may then be inserted into the joint capsule via the guide. A proximal end of the flexible drill is connected to a standard orthopedic power drill and a pilot hole is drilled in the glenoid rim. The flexible drill is then removed from the guide. A flexible inserter may then be inserted into the joint capsule via the curved guide to insert a suture anchor previously placed thereon into the pilot hole such as a Stryker Corp. 3.5 mm TwinLoop™ suture anchor. The flexible inserter is then removed from the guide. The guide is then removed from the cannula and the cannula removed (or alternatively, the guide is withdrawn from the surrounding tissue if no cannula is used).

The cannula may be included in the apparatus for inserting a suture anchor into an internal anatomical site such as a glenoid. The system may include a cannula for accessing an internal anatomical site and a curved hollow guide for insertion into the cannula. The guide has a proximal end and a distal end. A flexible obturator is insertable through the curved guide from its proximal end to its distal end. A flexible drill is also insertable through the curved guide from the proximal to the distal end. A flexible inserter is provided for inserting a suture anchor into a bore at the anatomical site formed by the flexible drill. The curved hollow guide distal end may have a tip with a pair of parallel edges formed by generally parabolic recesses in an aperture wall of the curved guide distal end. This type of distal end has a contour shaped to engage a scapular glenoid rim of a shoulder. The distal end of the curved hollow guide may also have at least one window extending through a wall thereof so the instruments inserted therein can be viewed. The window is spaced from the distal tip of the curved hollow guide a distance allowing the viewing of a proximal end of a suture anchor located adjacent the tip. The anatomical site may be a glenoid rim. The curved hollow guide may have a bend of 0° to 90°, and more specifically 0° to 25°.

In an alternative embodiment, the system for implanting an anchor into bone may include a cannulated guide comprising a proximal end, a distal end positionable proximate a bone, and a shaft extending between the proximal and distal ends, the shaft having a curved shape, a drill comprising a proximal end configured to receive torque, a rotary drilling head, and a flexible shaft extending between the proximal end and the rotary drilling head. The guide shaft permits passage of the rotary drilling head through the shaft of the cannulated guide. The flexible shaft of the drill comprises a plurality of discrete grooves, each of which extends around the shaft to provide a flexible transitional region, thereby dividing the shaft into a plurality of rigid segments separated by the flexible transitional regions.

In yet another embodiment, the system for implanting an anchor into bone, the system has a cannulated guide comprising a proximal end, a distal end positionable proximate a bone, and a curved shaft extending between the proximal and distal ends, a drill comprising a proximal end configured to receive torque, a distal rotary drilling head and a shaft extending between the proximal end and the rotary drilling head. The shaft comprises a flexible portion and permits passage of the rotary drilling head through the shaft of the cannulated guide. One of the drill and the cannulated guide comprises a stop feature shaped to interface with the other of the drill and the cannulated guide to adjustably control a maximum range of motion of the rotary drilling head through the cannulated guide. The stop feature may be threadably mounted on the drill proximal end.

BRIEF DESCRIPTION OF THE DRAWINGS

FIG. 2 shows one embodiment of a 25° standard orientation curved hollow guide of the present invention;

FIG. 3 shows one embodiment of a 25° rotated orientation curved hollow guide of the present invention;

FIG. 4 shows one embodiment of a 12° standard orientation curved hollow guide of the present invention;

FIG. 5 shows one embodiment of a 12° rotated orientation curved hollow guide of the present invention;

FIG. 6 shows one embodiment of a 0° hollow guide of the present invention;

FIG. 18A shows one embodiment of a suture anchor inserter for use with the guides of FIGS. 2-6;

FIG. 18B shows a cross-sectional view of the inserter of FIG. 18A;

FIG. 25 shows one of the guides of FIGS. 2-6 with the obturator removed.

FIG. 27 shows the inserter of FIG. 18A including an exemplary suture anchor for insertion through one of the guides of FIGS. 2-6 into the pilot hole of FIG. 26;

FIG. 28 shows yet another embodiment of a suture anchor inserter for use with the guides of FIGS. 2-6; and FIG. 28A shows one embodiment of a distal end of the suture anchor inserter of FIG. 28.

DETAILED DESCRIPTION

Figure 1:
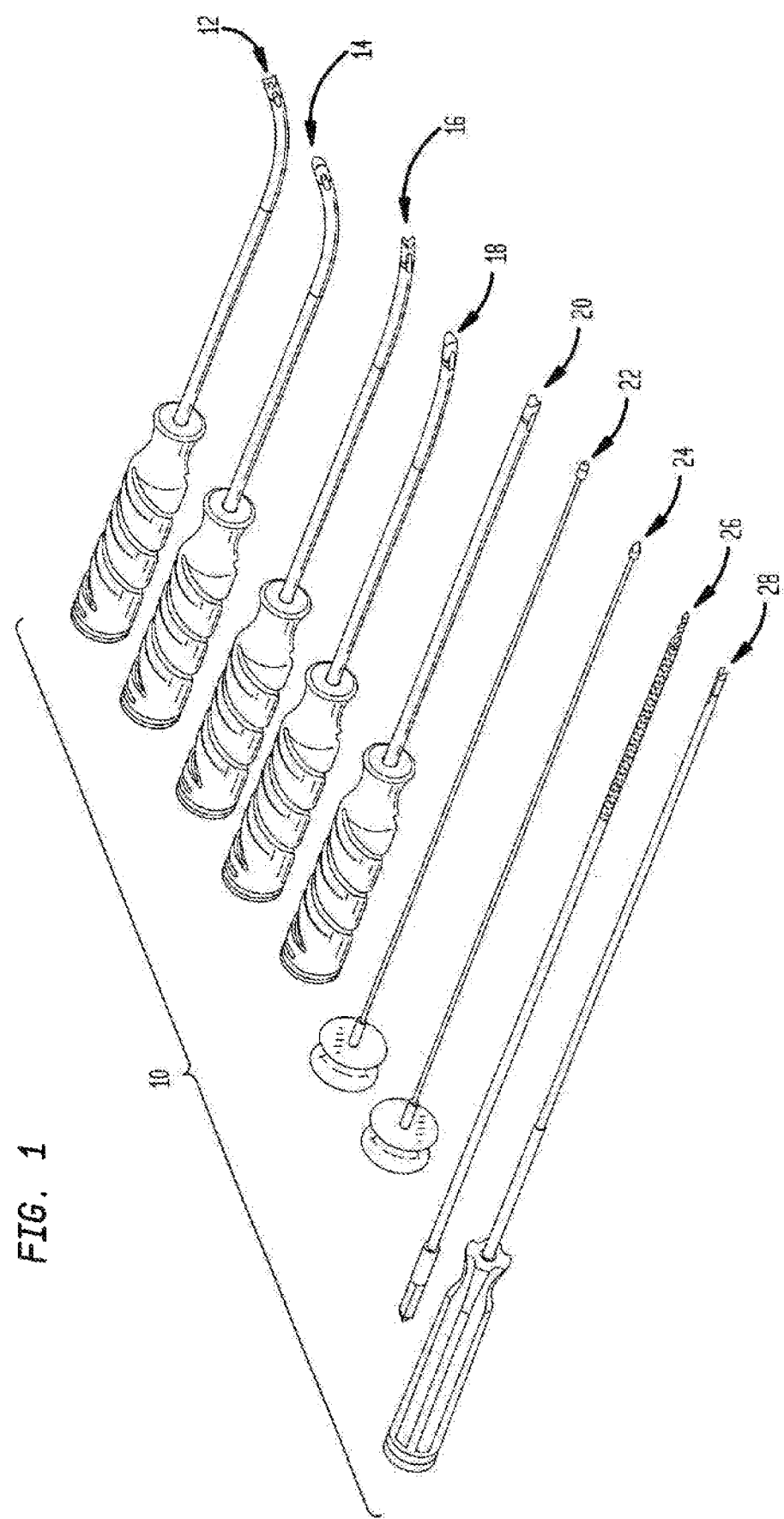
FIG. 1 shows a first embodiment of a suture anchor insertion system of the present invention.

Referring to FIG. 1 there is shown one embodiment of an instrumentation system of the present invention generally denoted as 10. The system includes various curved guides having a curved guide shaft with a curved angle of between about 0° and about 90°. Specifically, the curved angle may be about 0° to about 25°, though any other angle is envisioned depending on the application of the guide. The system may consist of, for example, a 25° rotated orientation curved guide 12, a 25° standard orientation curved guide 14, a 12° rotated orientation curved guide 16, a 12° standard orientation curved guide 18, and a 0° (i.e. straight) guide 20. In one example, the rotated orientation guides may be used on the posterior glenoid rim, and the standard orientation guides may be used on the anterior glenoid rim, though this may be reversed if desired. Furthermore, in an alternate example, the rotated orientation guides may be used within the posterior portal, and the standard orientation guides may be used within the anterior portal, or vice versa, depending upon the desires of the user and the surgical application. The 0° guide may be rotated 90° and used on the anterior or posterior glenoid rim. Bullet tip obturator 22 and a trocar tip obturator 24 may also be provided and may be used for insertion through the cannulated opening in each of the guides 12, 14, 16, 18 and 20. A flexible drill 26 may further be provided. The drill tip may be capable of drilling, for example, a 3.5 mm pilot hole. Finally a suture anchor inserter 28 may be provided which again has a flexible shaft and is capable of receiving, for example, a 5 mm suture anchor which may either be made of metal or a polymer such as polyetheretherketone (PEEK).

Referring to FIG. 2 there is shown a first embodiment of the 25° standard orientation curved guide 14 which includes a hollow tubular shaft 29 and handle 30 which is cannulated to allow the passage of the various other instruments of the system therethrough. FIG. 3 shows a first embodiment of a 25° rotated orientation curved guide 12 having a shaft 31 also attached to a handle 30. Guides 14 and 12 include a distal end 32, 34 respectively having edges 36, 38 defining an aperture opening to the hollow anterior of each of the curved guide shafts. Distal ends 32, 34 may include windows 42, in any form or shape, such as illustrated as elongated slats, in the walls of the shafts which allow the various instruments extending through the hollow interior of the shafts of the curved guides 12, 14 to be viewed. In one embodiment, a window 42 may be on at least one side of the distal end of each guide.

Likewise FIG. 4 shows a first embodiment of a 12° standard orientation curved guide 18. FIG. 5 shows a first embodiment of a 12° rotated orientation curved guide 16. Again, both guides 18 and 16 include shafts 44 and 46 which are tubular in shape and are received within cannulated handles 30. The shafts 44 and 46 are curved at 12° compared to the 25° curve of shafts 29 and 31. By this it is meant that the central axis of the straight part of the shaft adjacent the handle and the central axis at the tip 52, 54 of guides 18 and 16 form an angle of 12°.

Referring to FIG. 6 there is shown guide 20 having a hollow shaft 58 and cannulated handle 30 in which the cannulation through the shaft and the handle are co-axial with the shaft 58 being straight thus having a 0° angle between the shaft part adjacent handle 30 and a distal shaft end 62. While the standard and rotated orientations refer to the relative position of the aperture as to the curve of the shaft, it is understood that the guide 20 could have either orientation because the curve of the shaft is 0 degrees.

Figure 7:
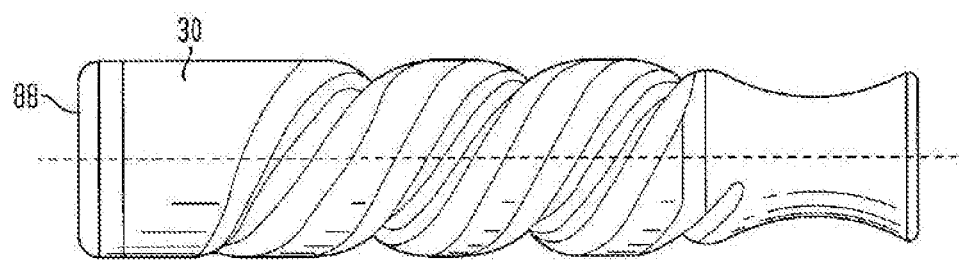
FIG. 7 shows one example of a handle which can be used with the guides of FIGS. 2-6.
Figure 8:
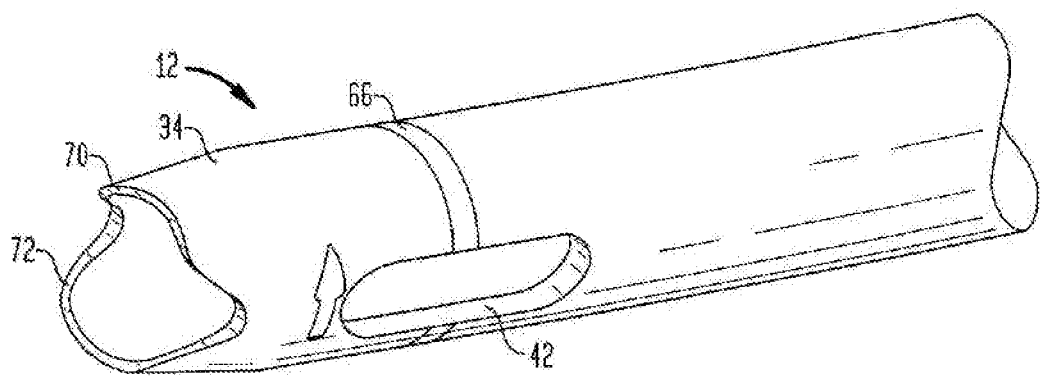
FIGS. 8-12 show multiple embodiments of the distal tip and aperture areas of the guides of FIGS. 2-6.

Referring to FIG. 7 there is shown one example of the handle 30 of guides 12, 14, 16, 18 and 20 which may be ergonomically designed having a helical groove formed for easy gripping. While the helically shaped handle 30 is shown, any handle design may be utilized as long as it has a cannulation adapted to receive the instruments 22, 24, 26 and 28 of system 10.

Figure 9:
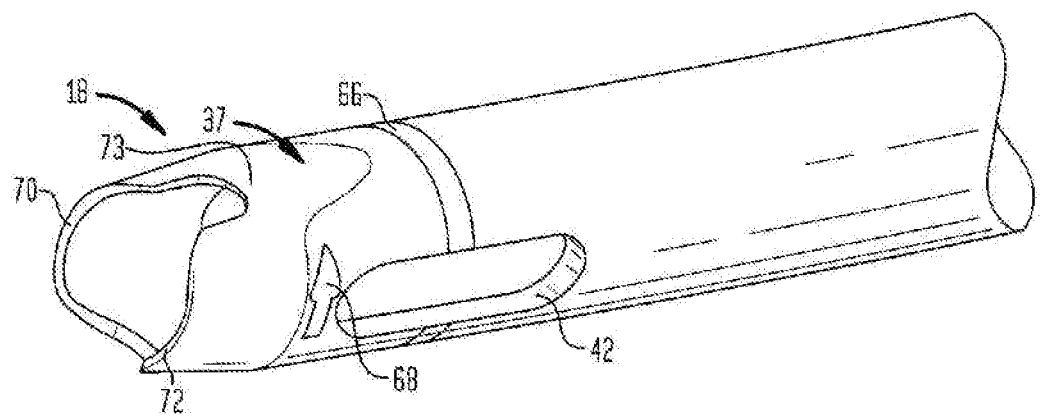
Figure 10:
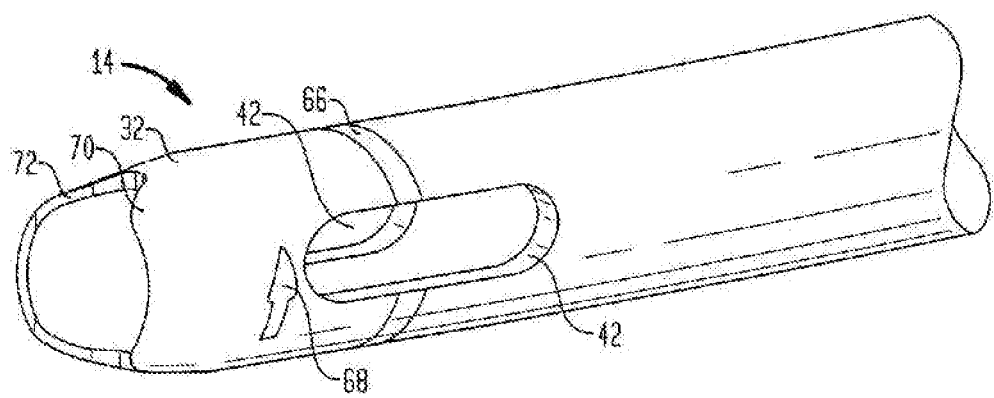
Figure 11:
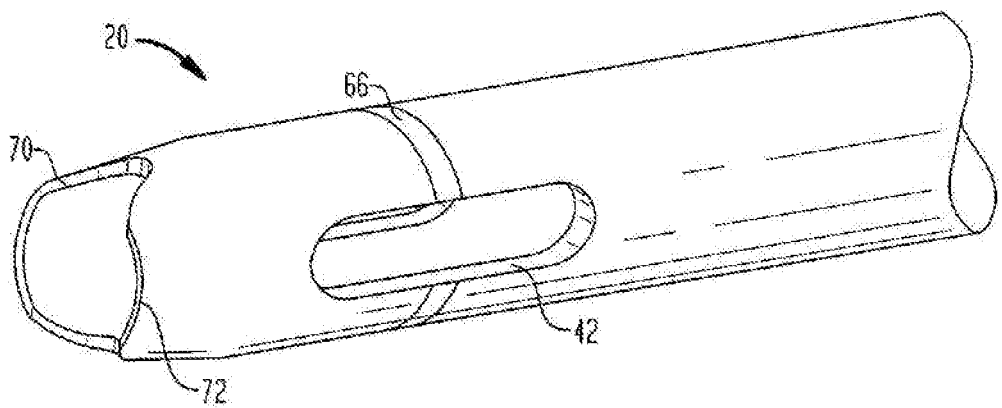
Figure 12:
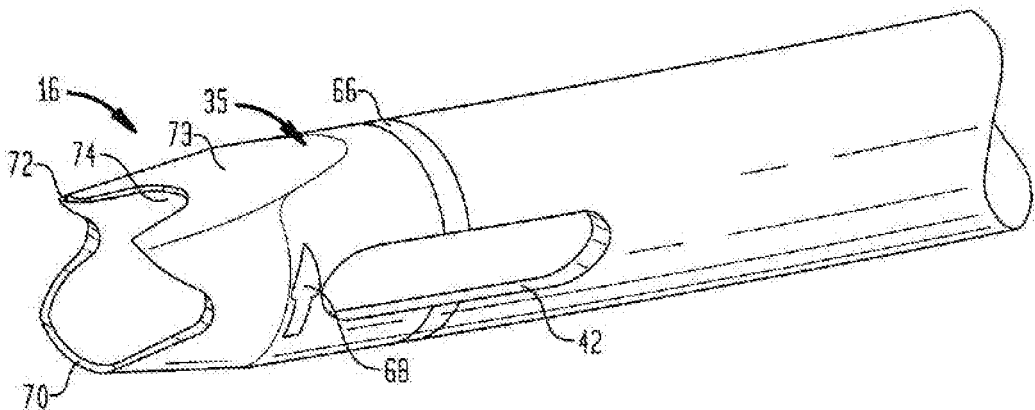

Referring to FIGS. 8-12, there are shown the various embodiments of the tips of the guides 12, 14, 16, 18 and 20. While each tip embodiment is designated to a specific guide, it should be understood that each tip can be used with each guide. The tip 32 of the 25° standard guide 14 is shown in FIG. 10 with the tip 34 of the 25° rotated guide 12 shown in FIG. 8. The 12° standard and rotated guides 18 and 16 are shown in FIGS. 9 and 12 respectively and have distal tips 37 and 35 respectively. The distal tip of the straight or 0° guide 20 is illustrated in FIG. 11. All the guide tips have a "parabolic" shape to, among other reasons, allow better engagement with the rim of the glenoid. The orientation of the "parabolic" with respect to the curved section on curved guides determine whether the orientation is standard or rotated, as is illustrated throughout the Figures. Each of the distal tips may have a laser marking 66 and, in the case of the curved guide, an arrow 68 pointing to the direction of curvature. Obviously the arrow 68 is unnecessary for the straight or 0° guide 20. Laser mark 66 indicates the desired depth of insertion of the instruments passing within the guides, and helps the user in achieving the specified depth of, for example, drilling into the bone or setting of the suture anchor. Each guide has edges 70 and 72 extending between the inner and outer walls of the hollow guide which edge surfaces are generally parabolic in shape. While the edges 70 and 72 form the parabolic shape are shown to be symmetric, they could be non-symmetric if such would better fit the anatomy.

Furthermore, edges 70 and 72 may include specific designs or dimensions depending on the requirements of anatomy or surgical procedure. For example, as illustrated in FIGS. 9 and 12, the aperture edge 70 or 72 may include a flattened portion 73. The portion 73 may assist in moving the guide through the cannula. This is particularly useful for the 12° guides, as shown, because the curve of the shaft may make it difficult for the parabolic shape to pass through the cannula. This may also be useful for the 25° guides, however, typically the 25° guide will be used without a cannula and will be inserted percutaneously because the curve of the shaft may not fit through a cannula. Moreover, as illustrated in FIG. 12, an edge 70 or 72 may include a cut-out 74. Cut-out 74 may further assist the passage of the curved guide through the cannula, while also providing sharpened points which may engage the bone and provide a stable base on which the guide 16 can rest.

Figure 13:
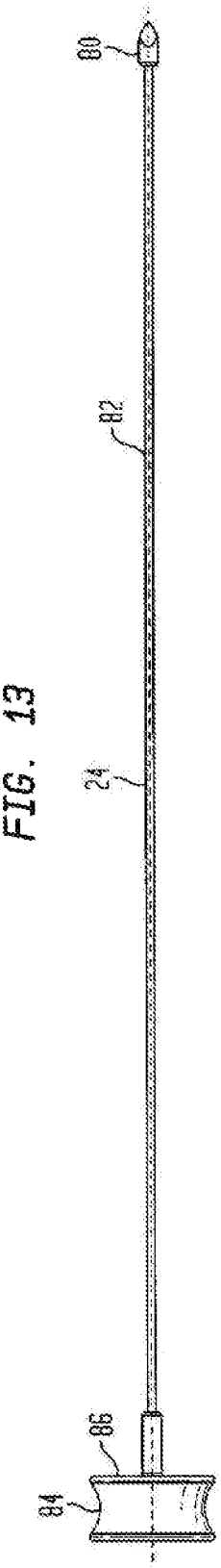
FIG. 13 shows one embodiment of a trocar tipped obturator for use with the guides of FIGS. 2-6.
Figure 14:
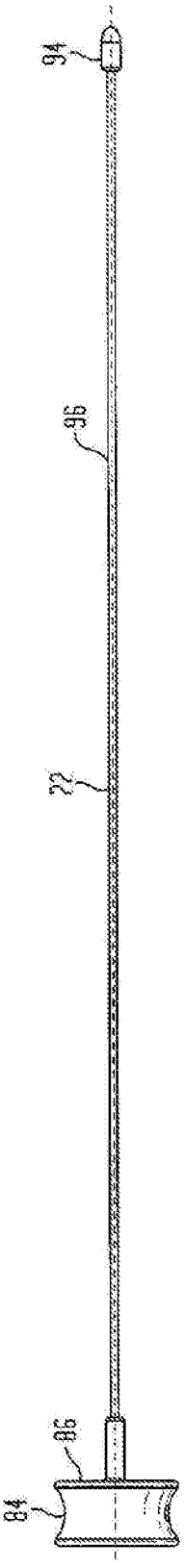
FIG. 14 shows one embodiment of a bullet tipped obturator for use with the guides of FIGS. 2-6.
Figure 16:
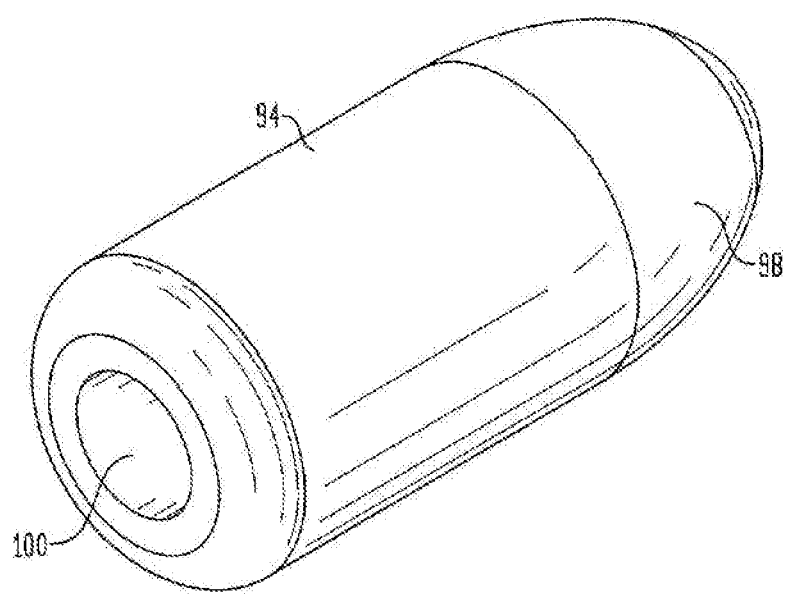
FIG. 16 shows a further embodiment of a bullet tip for use with the obturator of FIG. 14.
Figure 17:
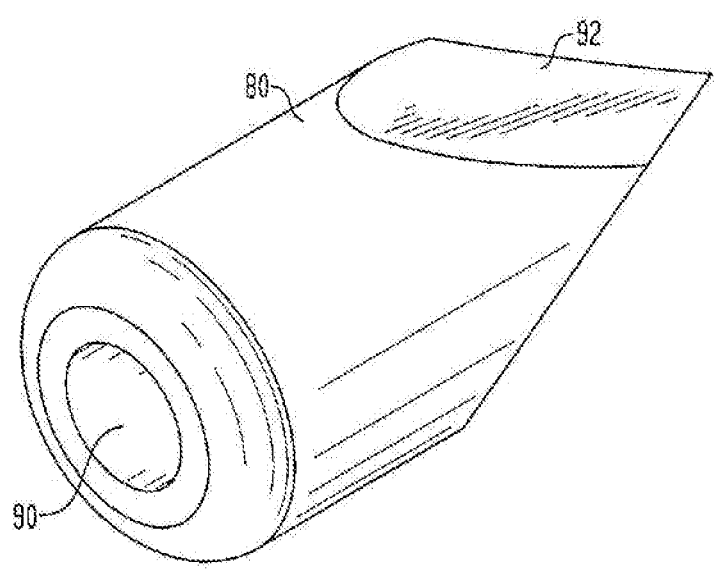
FIG. 17 shows a further embodiment of a trocar tip for use with the obturator of FIG. 13.

Referring to FIG. 13 there is shown one embodiment of an obturator 24 including a trocar tip 80. The obturator may be made of a flexible shaft 82 and a handle portion 84 with an adjustable stop surface 86 which can engage a proximal surface 88 of handle 30 as shown for example in FIG. 7. The shaft 82 may be made from nitinol with trocar tip 80 being made, for example, of titanium. One embodiment of tip 80 is shown enlarged in FIG. 17 and has a bore 90 for receiving nitinol shaft 82 and a sharpened point 92. Referring to FIG. 14 there is shown one embodiment of an obturator shaft 22 including a bullet tip 94 again with handle portion 84 having a stop surface 86. Obturator 22 again may include a nitinol shaft 96 on which bullet tip 94 is mounted. Tip 94 is shown in an enlarged view in FIG. 16 which has a typical bullet shaped point 98 and a bore 100 for receiving shaft 96. Both tips 80 and 94 may be welded to their respective shafts 82 and 96. The outer diameters of tip 80 and 94 are sized to be slidingly received within the hollow bore of guides 12, 14, 16, 18 and 20. The tips help prevent damage to the seal on the inner bore of the cannula. Also, trocar tip 80 may be used to cut through tissue in percutaneous applications, while bullet tip 94 may also push aside tissue when moving the guide within the body.

Figure 15:
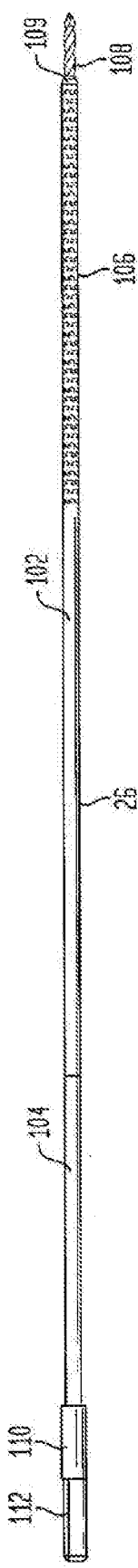
FIG. 15 shows one embodiment of a flexible drill for use with the guides of FIGS. 2-6.

Referring to FIG. 15 there is shown drill 26 which includes a shaft 102 which, in another embodiment, has a proximal solid portion 104 and a flexible portion 106. The flexible portion 106 is made by taking hypodermic metal tubing and forming a laser cut in the metal to a sufficient depth to allow flexing about the cut. The shaft 102 may be substantially cannulated and may include a thickness between an outer surface and an inner surface, such as would be the case with hypodermic metal tubing, for example. The laser cut may extend circumferentially around the outer surface of the hypodermic tubing and may have a wave or sinusoidal shape to enhance flexibility. For example, the laser cuts may merely score the outer surface, or may penetrate deeper into the thickness of the shaft. The flexible portion is then laser welded onto the solid rod of section 104. In a further embodiment, the laser cuts may pass completely through the tubing to form discrete portions of tubing which may be interlocked by the shape of the cuts, for example, like jig-saw puzzle pieces, such that sections 104 and 106 may be a single piece, and the laser cut may then be applied to the tubing at portion 106 to form the flexible portion. At the distal end of the flexible section 106 is a drill bit 108 which may be laser welded at point 109 to flexible portion 106. The drill bit 108 may have a diameter for producing a pilot hole to receive a desired suture anchor such as a 3.5 mm suture anchor. A proximal end 110 of flexible drill 26 includes a drive element 112 which may be inserted into a standard power drill chuck. Proximal end 110 also includes a stop feature for engaging surface 88 of handle 30 to limit the depth of a pilot hole drilled in bone.

Figure 19:
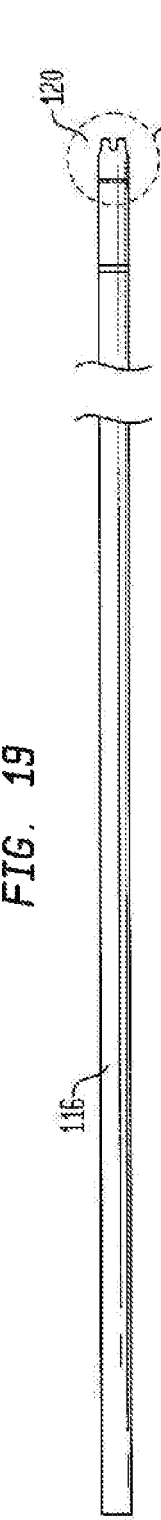
FIGS. 19 and 21 show multiple embodiments of the tip of the inserter of FIG. 18A with the tip shown in FIG. 21 being rotated 90° with respect to the tip shown in FIG. 19.
Figure 20:
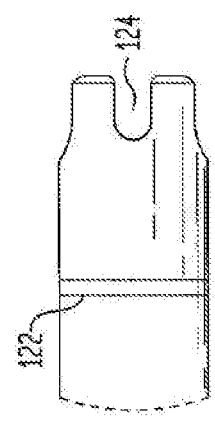
FIGS. 20 and 22 show enlarged areas A and B of the tips of FIGS. 19 and 21 respectively.
Figure 21:
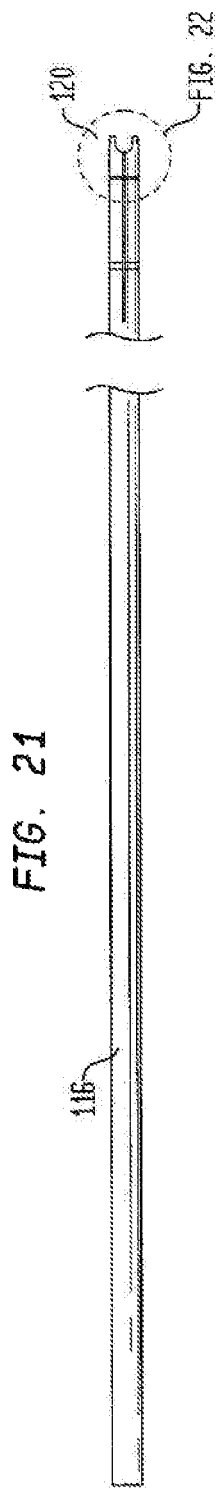
Figure 22:

Referring to FIGS. 18A-22 there is shown one embodiment of the flexible suture anchor inserter 28 of the present invention. Referring to FIG. 18A there is shown an elevation view of inserter 28 which can be seen in cross-section in FIG. 18B. Inserter 28 has a handle 114 which is cannulated as is the shaft portion 116. Referring to FIGS. 19 and 21, FIG. 19 illustrates one example of the distal end 120 of shaft 116 with FIG. 21 showing shaft 116 rotated 90° with respect to the view shown in FIG. 19. FIGS. 20 and 22 show enlarged views A and B of the distal end 120 including a laser marking 122 and u-shaped recessed areas 124 and 126. As shown in FIG. 22 the tip 120 may also include an axially extending laser marking 130. Marking 130 may show the orientation of the suture anchor attached to tip 120. For example, the vertical marking 130 may show the orientation of a suture eyelet on the suture anchor. Tips 120 including recesses 124, 126, are adapted to receive, for example, a 3.5 mm Stryker TwinLoop™ suture anchor. Of course the tip can be designed to be utilized with any desirable suture anchor. Suture (not shown), which may be attached to the suture anchor, may then be passed up through the cannulated shaft and handle. Alternatively, the suture may be positioned elsewhere relative to the suture anchor and inserter, as is known in the art.

FIGS. 28 and 28A illustrate another embodiment of a flexible suture anchor inserter 128. Similar to the construction of the flexible drill 26, above, a shaft portion 216 may include a solid portion 204 and a flexible portion 206. The flexible portion 206 is made using a length of hypodermic metal tubing, or the like, and forming a laser cut in the metal to a sufficient depth to allow flexing about the cut. The shaft 216 may be substantially cannulated and may include a thickness between an outer surface and an inner surface, such as would be the case with hypodermic metal tubing, for example. The laser cut may extend circumferentially around the outer surface of the hypodermic tubing and may have a wave, or sinusoidal shape to enhance flexibility. The cuts may, in another arrangement, be a single cut which moves along at least a portion of the shaft in a spiral pattern, like a thread on a screw. The laser cuts may be at any depth relative to the thickness of the shaft, such as, for example, cuts which merely score the outer surface, or cuts which may penetrate deeper into the thickness of the shaft. The flexible portion is then laser welded onto the solid rod of section 204. In a further embodiment, the laser cuts may pass completely through the tubing to form discrete portions of tubing which may be interlocked by the shape of the cuts, for example, like jig-saw puzzle pieces, such that sections 204 and 206 may be a single piece, and the laser cut may then be applied to the tubing at portion 206 to form the flexible portion. The cuts may be in a circumferential pattern, in a spiral pattern, or the like. At the distal end of the flexible section 206 is a tip 220, which may be laser welded at point 209 to flexible portion 206. Alternatively, tip 220 may be a unitary piece, along with portions 204 and 206, and is later machined as needed to accommodate a suture anchor. This interlocking flexible portion 206 may provide even stronger resistance to buckling when, for example, pressing the suture anchor into the pilot hole.

Figure 23:
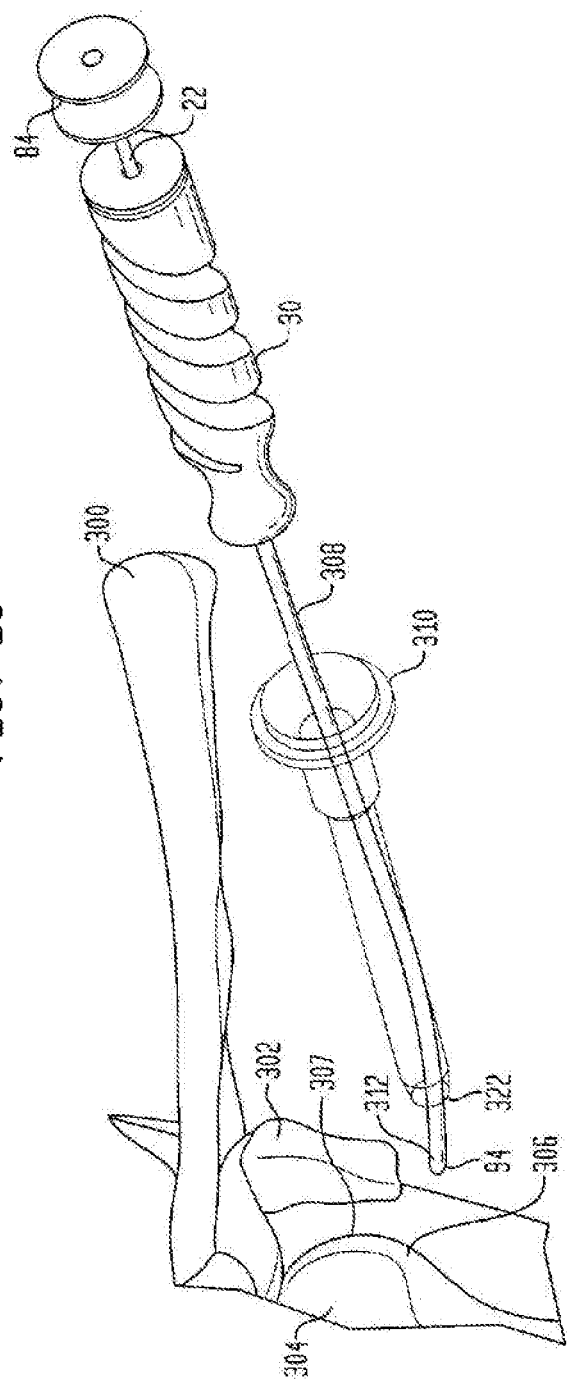
FIG. 23 shows a first embodiment of the insertion of one of the guides of the present invention into a shoulder joint including an obturator bullet tip for ease of insertion of the guide through a cannula for guiding the guides of the present invention into the joint area.
Figure 24:
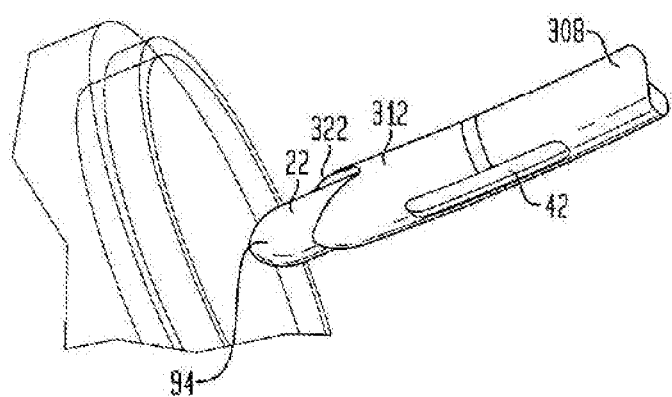
FIG. 24 shows an enlarged view of the obturator with a bullet tip as shown in FIG. 23.

The method of using the system 10 will now be explained. Referring to FIGS. 23 and 24 there is shown a schematic of the bones in the shoulder which include a clavicle 300, a coracoid process 302 and a proximal humerus 304. A head 307 of the proximal humerus 304 engages a glenoid 306. One guide chosen from guides 16, 18 and 20 may be placed in a cannula 310 such that a tip 312 of the guide is located adjacent the glenoid 306. Guides 12 and 14 may also be used in this method, but due to the 25° curvature, a cannula may not be used and percutaneous entry may be used instead (though of course the use of a cannula capable of handling the 25° curved angle may allow these guides to be used with a cannula). Likewise, any of guides 16, 18 and 20 may also be used percutaneously, without a cannula. An obturator 22 having a bullet shaped tip is shown in this method. Obturator 24 can be used if a trocar tip 80 is required, especially for percutaneous entry. The cannula which may be used with this method may be any cannula known in the art suitable for use with the guides of the present invention.

Figure 26:
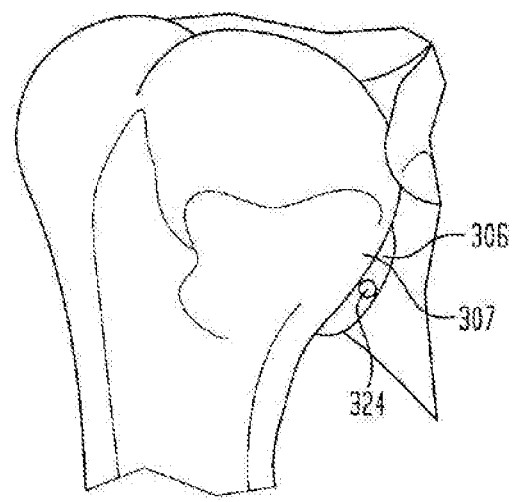
FIG. 26 shows a pilot hole drilled in the rim of the glenoid using the drill of FIG. 15 inserted through one of the guides of FIGS. 2-6.

Referring to FIG. 24 there is an enlarged view of the distal tip 312 of guide 308 with the bullet tip 94 of the obturator 22 extending beyond the edges 322 of tip 312. As shown in FIG. 25 after the tip 312 of guide 308 is properly located adjacent the glenoid 306, the obturator 22 is removed with the guide 308 positioned as shown in FIG. 25. Using the laser marked arrows 68 which may be pointed towards the curved section of the guide therefore allows the surgeon to orient the bend in a manner to place the parabolic shaped edge 322 of the distal tip portion 312 on the glenoid rim 306 at an appropriate location to perform the repair. The flexible drill 26 is then inserted through guide 308 and a pilot hole 324 is drilled in the glenoid rim 306 as shown in FIG. 26. The drill tip 108 is visible in windows 42 of tip 312 prior to drilling the hole 324. The flexible drill 26 is then removed from the cannulated bore in drill guide 308.

Referring to FIG. 27, a suture anchor 330 is then placed on the tip 120 of an inserter 28 which again is placed through the cannulation of handle 30 and through the guide 308 into pilot hole 324 in the glenoid rim 306. Again the suture anchor would be visible in window 42 of tip 312, and laser markings 66, 122 and 130 may be used to orient the suture anchor to a proper depth into the bone and proper radial alignment (i.e., rotational alignment of suture eyelets) dependent upon a particular application. After the suture anchor is firmly in position on rim 306 the inserter 28 is removed from guide 308. Additional suture anchors may be implanted in the rim as desired. After the installation of suture anchors is complete the guide 308 and the cannula 310 are removed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A guide for accessing an internal anatomical site comprising:
   a hollow shaft having a longitudinal axis, an inner wall, an outer wall, a proximal end, and a distal end, the distal end having an edge extending between the inner and outer walls, the edge including a first sharpened point and a second sharpened point, and the distal end including a flattened surface, wherein the flattened surface forms a portion of the outer wall including the first and second sharpened points, and wherein the guide is adapted to receive a flexible drill.

2. The guide of claim 1, wherein the edge includes a first edge and a second edge, and the first edge is positioned opposite the second edge, the first edge having a first shape and the second edge having a second shape, wherein the first shape includes the first and second sharpened points and is different from the second shape.

3. The guide of claim 2, wherein the flattened surface extends along at least a portion of the outer wall to the first edge.

4. The guide of claim 2, wherein the shaft includes a curvature along at least a portion of the longitudinal axis, the first edge circumferentially aligning with an inner curve of the curvature.

5. The guide of claim 4, wherein the first shape of the first edge includes a cut-out that defines a parabolic aperture, wherein the cut-out aligns with one of an outer curve or an inner curve of the curvature.

6. The guide of claim 5, wherein the parabolic aperture is positioned along the longitudinal axis.

7. The guide of claim 5, wherein the parabolic aperture is configured to mate with anatomical features of a glenoid.

8. The guide of claim 4, wherein the first shape of the first edge includes a cut-out that defines a parabolic aperture, wherein the cut-out is offset from an outer curve and an inner curve of the curvature.

9. The guide of claim 1, wherein the distal end terminates in the edge.

10. The guide of claim 1, wherein the shaft has a curved angle of about 0 degrees to about 90 degrees.

11. The guide of claim 1, wherein the shaft has a curved angle of about 0 degrees to about 25 degrees.

12. A system comprising:
the guide of claim 1; and
the flexible drill capable of passing through the guide.

13. A system comprising:
a guide for accessing an internal anatomical site comprising:
a hollow shaft having a longitudinal axis, an inner wall, an outer wall, a proximal end, and a distal end, the distal end including a first edge and a second edge defining a distal opening, the first edge including a cut-out positioned between a first sharpened point and a second sharpened point, and the outer wall including a flattened portion including the first and second sharpened points and the cut-out; and
a flexible drill capable of passing through the guide.

14. The system of claim 13, wherein the cut-out has a parabolic shape.

15. The system of claim 13, wherein the flattened portion extends along at least a portion of the outer wall to the first edge, wherein the cut-out is along at least part of the flattened portion.

16. The system of claim 13, wherein the shaft includes a curvature along at least a portion of the longitudinal axis and the cut-out of the first edge aligns with one of an outer curve or an inner curve of the curvature.

17. The system of claim 13, wherein the shaft includes a curvature along at least a portion of the longitudinal axis and the flattened portion aligns with an inner curve of the curvature.

18. The system of claim 13, wherein the first edge is positioned opposite the second edge, the first edge having a first shape and the second edge having a second shape, wherein the first shape includes the first and second sharpened points and is different from the second shape.

19. The system of claim 13, wherein the flattened portion extends along at least a portion of the outer wall to the first edge.

20. The system of claim 19, wherein the cut-out is positioned along the longitudinal axis.

* * * * *